US009734577B2

(12) United States Patent
Lagae et al.

(10) Patent No.: US 9,734,577 B2
(45) Date of Patent: Aug. 15, 2017

(54) ANALYSIS AND SORTING OF OBJECTS IN FLOW

(71) Applicants: IMEC, Leuven (BE); Katholieke Universiteit Leuven, KU LEUVEN R&D, Leuven (BE)

(72) Inventors: Liesbet Lagae, Leuven (BE); Peter Peumans, Herfelingen (BE); Kris Verstreken, Schilde (BE); Dries Vercruysse, Sint Andries (BE); Chengxun Liu, Leuven (BE)

(73) Assignees: IMEC, Leuven (BE); Katholieke Universiteit Leuven, KU Leuven R&D, Leuven (BE)

( * ) Notice: Subject to any disclaimer, the term of this patent is extended or adjusted under 35 U.S.C. 154(b) by 0 days.

(21) Appl. No.: 15/352,311

(22) Filed: Nov. 15, 2016

(65) Prior Publication Data

US 2017/0061619 A1 Mar. 2, 2017

Related U.S. Application Data

(63) Continuation of application No. 14/363,373, filed as application No. PCT/EP2012/074865 on Dec. 7, 2012, now Pat. No. 9,495,742.

(30) Foreign Application Priority Data

May 2, 2012 (EP) .................................. 12166436

(51) Int. Cl.
*G06K 9/00* (2006.01)
*G06T 7/00* (2017.01)
(Continued)

(52) U.S. Cl.
CPC ......... *G06T 7/0012* (2013.01); *G01N 15/147* (2013.01); *G01N 15/1434* (2013.01);
(Continued)

(58) Field of Classification Search
CPC ........... G01N 15/1484; G01N 15/1436; G01N 2015/149; G06K 9/6267;
(Continued)

(56) References Cited

U.S. PATENT DOCUMENTS

| 7,210,937 B1 | 5/2007 | Raghu |
| 8,610,085 B2 | 12/2013 | Patt |

(Continued)

OTHER PUBLICATIONS

Moon, SangJun et al., "Integrating Microfluidics and Lensless Imaging for Point-of-Care Testing", Biosensors and Bioelectronics, vol. 24, Apr. 2, 2009, pp. 3208-3214.
(Continued)

*Primary Examiner* — Daniel Mariam
(74) *Attorney, Agent, or Firm* — McDonnell Boehnen Hulbert & Berghoff LLP

(57) ABSTRACT

A device and method for sorting objects immersed in a flowing medium are disclosed. An example device comprises a holographic imaging unit comprising one or more holographic imaging elements, a fluid handling unit comprising one or more microfluidic channels configured to conduct flowing medium along a corresponding holographic imaging element and at least one microfluidic switch arranged downstream of an imaging region in the microfluidic channel configured to direct objects in the flowing medium into a one of a plurality of outlets. The example device also comprises a processor configured to determine real-time characterizations of holographic diffraction images obtained for the moving objects. The processing unit is
(Continued)

further configured to control the at least one microfluidic switch in response to the real-time characterizations.

20 Claims, 7 Drawing Sheets

Related U.S. Application Data

(60) Provisional application No. 61/567,817, filed on Dec. 7, 2011.

(51) Int. Cl.

| | | |
|---|---|---|
| *G01N 15/14* | (2006.01) | |
| *G03H 1/22* | (2006.01) | |
| *G06K 9/46* | (2006.01) | |
| *G06K 9/62* | (2006.01) | |
| *G06T 7/20* | (2017.01) | |
| *G03H 1/00* | (2006.01) | |
| *G03H 1/04* | (2006.01) | |

(52) U.S. Cl.
CPC ..... *G01N 15/1436* (2013.01); *G01N 15/1463* (2013.01); *G01N 15/1484* (2013.01); *G03H 1/0443* (2013.01); *G03H 1/22* (2013.01); *G06K 9/46* (2013.01); *G06K 9/6267* (2013.01); *G06T 7/20* (2013.01); *G01N 15/1475* (2013.01); *G01N 2015/149* (2013.01); *G01N 2015/1445* (2013.01); *G03H 2001/005* (2013.01); *G03H 2001/0033* (2013.01); *G03H 2001/0447* (2013.01); *G03H 2222/33* (2013.01); *G03H 2226/13* (2013.01); *G06T 2207/30004* (2013.01)

(58) Field of Classification Search
CPC ......... G06T 2207/30004; G06T 7/0012; G06T 7/20; G06N 2015/1445
USPC ........ 382/128, 133, 191, 195, 224; 356/341, 356/456, 457
See application file for complete search history.

(56) References Cited

U.S. PATENT DOCUMENTS

| 8,778,279 | B2 | 7/2014 | Durack |
|---|---|---|---|
| 2005/0179968 | A1 | 8/2005 | Molteni et al. |
| 2008/0213821 | A1 | 9/2008 | Liu et al. |
| 2009/0003681 | A1 | 1/2009 | Ortyn et al. |
| 2011/0136165 | A1 | 6/2011 | Vojnovic et al. |
| 2013/0222547 | A1 | 8/2013 | Van Rooyen et al. |
| 2013/0258091 | A1 | 10/2013 | Ozcan et al. |

OTHER PUBLICATIONS

Moon, SangJun et al., "Lensless Imaging for Point-of-Care Testing", 31st Annual International Conference of the IEEE EMBS, Minneapolis, Minnesota, Sep. 2-6, 2009, pp. 6376-6379.
Eisenstein, Michael, "Divide and Conquer", Nature, vol. 441, Jun. 29, 2006, p. 1179.
Chen, C.C. et al., "Micromachined Bubble-Jet Cell Sorter With Multiple Operation Modes", Sensors and Actuators, B vol. 117, Jul. 7, 2006, pp. 523-529.
Bluma, Ame et al., "In-Situ Imaging Sensors for Bioprocess Monitoring: State of the Art", Anal Bioanal Chem, vol. 398, Sep. 12, 2010, pp. 2429-2438.
Camisard, V. et al., "Inline Characterization of Cell Concentration and Cell Volume in Agitated Bioreactors Using In Situ Microscopy: Application to Volume Variation Induced by Osmotic Stress", Biotechnology and Bioengineering, vol. 78, No. 1, Apr. 5, 2002, pp. 73-80.
Joeris, Klaus et al., "In-Situ Microscopy: Online Process Monitoring of Mammalian Cell Cultures", Cytotechnology, vol. 38, Mar. 31, 2002, pp. 129-134.
Rehbock, Christoph et al., "Development of a Flow-Through Microscopic Multitesting System for Parallel Monitoring of Cell Samples in Biotechnological Cultivation Processes", Journal of Biotechnology, vol. 150, Jul. 8, 2010, pp. 87-93.
Went, Philip et al., "Frequent EpCam Protein Expression in Human Carcinomas", Human Pathology, vol. 35, No. 1, Jan. 2004, pp. 122-128.
Seo, Sungkyu et al., "Lensfree Holographic Imaging for On-Chip Cytometry and Diagnostics", Lab on a Chip, vol. 9, Mar. 21, 2009, pp. 777-787.
Aus Der Wiesche, S. et al., "Dynamics in Microfluidic Systems With Microheaters", Technical Proceedings of the 1999 Conference on Modelling and Simulation of Microsystems, Apr. 1999, pp. 510-513.
Hou, Jian-Mei et al., "Circulating Tumor Cells, Enumeration and Beyond", Cancers, vol. 2, Jun. 9, 2010, pp. 1236-1250.
Vona, Giovanna et al., "Technical Advance. Isolation by Size of Epithelial Tumor Cells. A New Method for the Immunomorphological and Molecular Characterization of Circulating Tumor Cells", American Journal of Pathology, vol. 156, No. 1, Jan. 2000, pp. 57-63.
Ijsselmuiden, Alexander J.J. et al., "Circulating White Blood Cells and Platelets Amplify Oxidative Stress in Heart Failure", Nature Clinical Practice, Cardiovascular Medicine, vol. 5, No. 12, Dec. 2008, pp. 811-820.

ANALYSIS AND SORTING OF OBJECTS IN FLOW

CROSS-REFERENCE TO RELATED APPLICATIONS

The present application is a continuation of U.S. patent application Ser. No. 14/363,373 filed Jun. 6, 2014, which is a U.S. national stage entry of International Application Serial No. PCT/EP2012/074865 filed Dec. 7, 2012, which claims priority to European Patent Application No. 12166436.1 filed May 2, 2012 and to U.S. Provisional Patent Application No. 61/567,817 filed Dec. 7, 2011, the contents of each of which are hereby incorporated by reference.

FIELD OF THE INVENTION

The invention relates to the field of cell analysis and sorting. More specifically it relates to the field of analysis and sorting of biological cells in a fluid.

BACKGROUND OF THE INVENTION

State of the art methods for cell sorting, which perform sorting of a heterogeneous mixture of biological cells into two or more containers based upon the specific light scattering and/or fluorescent characteristics of each cell, include fluorescence-activated cell sorting (FACS) and methods based on flow cytometry. Such sorting may consist of two phases, e.g. a first phase may be a so-called discrimination phase, in which a cell is classified based on the fluorescence and/or light scattering properties of the cell, while the second phase may be a so-called fractionation phase, in which the fluid stream is separated into charged droplets which can be deflected mechanically or electrostatically in order to divert the droplets into different bins. FACS has been the workhorse of biology researchers, which may be due to a number of reasons. For example, FACS has a high single cell level sensitivity and therefore may be capable of detecting cell surface markers at the single cell level, which may be largely due to the excellent sensitivity of the fluorescence detection. Furthermore, FACS has a high throughput of sorting and/or counting, which allows population-averaged single cell data. Today's high speed sorter systems can analyze up to 100,000 events per second. This throughput may be limited at least by the speed at which droplets can be deflected. FACS furthermore has the ability to track multiple parameters. Modern FACS instruments may have multiple lasers and detectors, adapted for versatile multispectral fluorescent staining applications. FACS systems are being used in a variety of applications discriminating cells based on size, morphology, cell pigments, protein expression level, fluorescent probes for in situ hybridization to visualize one or more specific regions of the genome inside the cell, e.g. via the so-called Flow-FISH, intracellular and nuclear protein markers, Green Fluorescent Proteins, pH, calcium stainings, etc. It may be possible to transport particular embodiments of this cell sorter between locations quickly, e.g. so that it could be a part of mobile system.

Modern FACS systems may have the disadvantage of a large equipment size and high cost, contamination between different samples, the serial nature of the sorting and low cell viability after ejection. There also exists a trade-off between the sorting speed, the purity rate and the recovery rate. Especially in modern cancer and immunology research, it may be important to recover all of the cells from the cell sorter with the highest achievable purity rate.

Microfluidic FACS systems bring miniaturization and disposability to cell sorting. Microfluidic FACS systems are generally perceived as slower than the macroscopic versions, see e.g. Nature Vol. 441, pg. 1179, but easier to parallelize. For example, IMT (Santa Barbara) has developed a rare cell purification system that uses 32 parallel channels with tiny micromechanical valves, optics and electromagnetic actuation to divert cells for rapid collection following detection of appropriate fluorescent markers. Cytonome has built an inventive microfluidic switch providing cell sorting of 2000 cells per second per channel by using 144 concurrently operating microfluidic sorters. Such a switch may be able to reach a sorting speed of 288,000 cells per second.

The United States patent application US 2008/213821 also discloses such a FACS device for sorting objects in a flowing medium. This device comprises a fluid handling unit comprising a plurality of microfluidic channels, which comprise a detection region for conducting flowing medium along a corresponding detector and a microfluidic switch arranged downstream of the detection region for controllably directing each object in the flowing medium to a plurality of outlets. Furthermore, a real-time characterization of detection signals obtained for each of the objects when passing through the detection region for controlling the microfluidic switch is described. In-flow imaging systems are also known in the art, e.g. the system disclosed by Amnis in US 2009/003681. This system uses conventional optics, e.g. a collection lens, a light dispersing element, an imaging lens and a CCD detector, to perform cell imaging in flow for diagnostic purposes. A time delay integration approach may be used for providing improved images of fast moving objects. This may result in high resolution images from which cell characteristics can be derived. For example, the Amnis system may be able to image up to 4000 cells per second.

Furthermore, a lens-free imaging system may be known, e.g. from Lab Chip, 2009, 9, 777-787. This paper discloses a lens-free holographic cytometer and an imaging and reconstruction method that results in an improvement of the reconstructed images with much richer texture information from the digitally processed holographic images. The system may be used for characterization and counting of cells statically present on a CMOS chip. This paper demonstrates that it is possible to perform identification or characterization of a heterogeneous cell solution on a chip based on pattern recognition of the holographic diffraction pattern of each cell type. The paper proposes the use these principles of lens-free imaging to do in-flow cell imaging at a very high speed.

However, the systems described above may not be appropriate for in-flow analysis and sorting of cells.

The described lens-free system is a static system for the analysis of cells. The cells are present in a micro-fluidic device; however, the cells are not in-flow. A different architecture and methodology is required to analyze cells in-flow.

The in-flow imagers described above require bulky conventional optics making them costly, expensive and not suitable for transport.

However, there remains a need for an in-flow cell analyzing/sorting system which is capable of a high throughput, which is flexible in terms of difference between cells under investigation, and which is reliable, easy-to use and also compact. Such systems with these properties are not currently available.

SUMMARY OF THE INVENTION

It is an object of embodiments of the present invention to provide fast and efficient sorting of objects in a flowing medium.

The above objective is accomplished by a method and device according to embodiments of the present invention.

The present invention relates to a device for sorting objects immersed in a flowing medium, the device comprising a holographic imaging unit comprising a plurality of holographic imaging elements for providing a plurality of holographic diffraction images, a fluid handling unit comprising a plurality of microfluidic channels, the microfluidic channels comprising an imaging region for conducting flowing medium along a corresponding holographic imaging element for imaging moving objects, e.g. fast moving objects, immersed in said flowing medium. For example, the holographic imaging unit may be adapted for imaging more than 500 passing objects per second, e.g. 1000 passing objects per second. For example, the holographic imaging unit may be adapted for imaging objects which move through the imaging region at a velocity of 1 cm/s or higher. The microfluidic channels furthermore comprise a microfluidic switch arranged downstream of said imaging region for controllably directing each object in the flowing medium into a selected one of a plurality of outlets, and a processing unit adapted for real-time characterization of the holographic diffraction image obtained for each of said objects when passing through any of said imaging regions, said characterization taking into account at least one predetermined object type signature, the processing unit furthermore being adapted for controlling the microfluidic switch downstream of said imaging region in response to said characterization.

The device according to embodiments of the present invention may further comprise synchronization means for generating a synchronization signal representative of detected presence of each object in the flowing medium upstream of each of said imaging regions and/or representative of detected presence of each object in the flowing medium upstream of the microfluidic switch. The processing unit may be arranged for performing the real-time characterization in response to the synchronization signal. The synchronization means may be incorporated in the holographic imaging elements. The synchronization means may be incorporated in the microfluidic channels.

The synchronization means may comprise a photodetector for receiving light modulated by, e.g. reflected by or transmitted through, the object. The synchronization means may comprise at least one electrode for detecting an electrical signal affected by the object.

Furthermore, the holographic imaging elements may be adapted for receiving and processing the synchronization signal from said synchronization means.

In embodiments, each of the plurality of microfluidic channels may further comprise a meandering segment arranged between the imaging region and the microfluidic switch for delaying the transition of each of the objects from the imaging region to the microfluidic switch while said real-time characterization is performed.

The plurality of microfluidic channels may be arranged in a cascade, such that at least one outlet of at least one first microfluidic channel feeds said flowing medium into at least one second microfluidic channel.

The holographic imaging unit may comprise a CMOS or CCD image sensor. In embodiments of the present invention, each microfluidic channel in the imaging region may furthermore be arranged at an angle with respect to the grid alignment of the CMOS or CCD image sensor. The processing unit may be adapted for constructing a super-resolution holographic diffraction image from a plurality of holographic diffraction images obtained for each of the objects in flow.

The device may furthermore comprise a plurality of fluorescence imaging elements for providing a plurality of fluorescence images. The imaging regions may furthermore be adapted for conducting flowing medium along a corresponding fluorescence imaging element of the plurality of fluorescence imaging elements. The processing unit may be adapted for real-time characterization of the holographic diffraction image and fluorescence image obtained for each of the objects when passing through the imaging regions. Each of the plurality of fluorescence imaging elements may comprise a multi-spectral filter assembly. Each of the plurality of fluorescence imaging elements may be used to provide a plurality of fluorescence sensing signals for each of the objects when passing through the imaging regions.

The holographic imaging elements may be adapted for detecting the presence of an object in the flowing medium and for providing holographic diffraction image data in response to said detection.

The microfluidic channels furthermore may comprise a focusing unit for concentrating said objects in a central region of the flowing medium in said imaging region.

The processing unit may comprise a Graphics Processing Unit, a Field Programmable Gate Array and/or an Application Specific Integrated Circuit.

The fluid handling unit furthermore may comprise an inlet for distributing said flowing medium over at least two of said plurality of microfluidic channels.

The plurality of outlets may be adapted for spotting objects on a removable carrier.

The holographic imaging unit may comprise at least one at least partially coherent pulsed light source for illuminating the flowing medium.

The at least one at least partially coherent pulsed light source may comprise a laser or a Light Emitting Diode optically coupled to a pinhole.

The at least one at least partially coherent pulsed light source may comprise a plurality of light sources configured for illuminating the flowing medium from different angles.

The holographic imaging unit may comprise an image sensor, wherein said holographic imaging unit comprises at least one polarizer optically coupled to the light source and to the image sensor and configured to select a polarization of light.

The partially coherent light sources may comprise or consist of light sources with one or multiple wavelengths.

In a device according to embodiments of the present invention, a pinhole aperture may be arranged on each microfluidic channel for creating a partially coherent pulsed light source.

Multiple pinhole apertures may be arranged on the microfluidic channel for creating multiple point sources.

The microfluidic switches may comprise thermally or piezo-electrically driven flow deflection means.

The microfluidic switches may comprise micro-heaters for generating vapor bubbles for displacing objects in said flowing medium.

The microfluidic switches may comprise a fluidic side chamber which volume can be adjusted by piezoelectric or thermal actuator to change the trajectory of the object in the microfluidic channel. The microfluidic switches may comprise a fluidic side chamber which volume can be adjusted by an externally actuated moveable membrane to change the trajectory of the object in the microfluidic channel.

The microfluidic switches may comprise a plurality of electrode elements electrically connected to an alternating current driving means for changing the trajectory of the object by dielectrophoresis.

The microfluidic switches may comprise a plurality of ultrasonic transducers for changing the trajectory of the object by acoustic radiation force.

The present invention also relates to the use of a device as described above for sorting cells from a biological specimen.

The present invention furthermore relates to a method for sorting objects immersed in a fluid, the method comprising
  introducing a flow of said fluid into a plurality of microfluidic channels, in which the microfluidic channels comprise an imaging region;
  recording a holographic diffraction image of the object when passing through any of said imaging regions;
  characterizing the holographic diffraction image obtained for each of said objects when passing through any of said imaging regions in real-time, said characterization taking into account at least one predetermined object type signature; and
  steering each object into an outlet, said outlet being selected from a plurality of outlets as a function of said characterization for said object.

The recording, characterizing and steering may be performed in parallel for a plurality of microfluidic channels.

The recording may comprise evaluating whether the object is passing through the imaging region.

The recording may comprise detecting the presence of the object in the flowing medium upstream of the imaging region, and the characterizing the holographic diffraction image may be performed in response to said detected presence.

Characterizing the holographic diffraction image may comprise comparing said holographic diffraction image with at least one stored reference hologram representing an object type of interest.

Characterizing the holographic diffraction image may comprise auto-correlating a plurality of holographic diffraction images in order to identify differences between objects.

Characterizing the holographic diffraction image may comprise performing at least a partial digital spatial reconstruction of the imaged object.

A high speed cell analysis and sorting device according to embodiments of the present invention is suitable for in-flow cell analyzing and sorting. It is flexible in terms of difference between cells under investigation. It is reliable, easy to use and compact.

It is an advantage of embodiments of the present invention that a system and method are provided for obtaining digital images of biological specimens in flow. The biological specimen may be fractionated based on the digital images.

It is an advantage of embodiments of the present invention that objects in flow are classified taking into account the geometry and complexity of objects in flow by characterizing these objects in two or three dimensions, e.g. in contrast to single pixel optical detection.

It is an advantage of embodiments of the present invention that a sample may be fractionated in real time.

It is an advantage of embodiments of the present invention that biological cells, micro-organisms or part of microorganisms such as pathogens, cell lysates endosomes and organelles may be sorted taking into account different dimensions and/or morphologies.

It is an advantage of embodiments of the present invention that a throughput of at least 1.000 objects per second per channel may be achieved, for example 20.000 cells per second per channel or even higher.

It is an advantage of embodiments of the present invention that a high content may be provided, e.g. digital images of cells may be obtained via holographic imaging rather than single photodetector-based signals. Such high content may provide a suitable input for accurate sorting, e.g. classification of cells.

It is an advantage of embodiments of the present invention that a high throughput may be provided, For example cells may be processed at speeds similar to or higher than microfluidic systems known in the art, e.g. FACS systems.

It is an advantage of embodiments of the present invention that continuous monitoring may be provided, e.g. a continuous analysis and sorting of a flow of objects. Therefore, a large amount of cells may be sampled continuously, which may improve the statistical relevance of the information gained during analysis or from subsequent processing and analysis of the sorted output.

It is an advantage of embodiments of the present invention that user definable and flexible methods and systems are provided that can differentiate cells or other bio-specimen based on one or more properties derivable from holographic images. Such properties may relate to morphology, size, pigmentation or fluorescent properties such as coming from epithelial or nuclear markers of choice. This flexibility may allow modifying the system for cell counts, size analysis, growth curves or other morphological analysis by simple user defined software settings without the need for adapting the optical path.

It is an advantage of embodiments of the present invention that a simple method is provided and a system that is easy to use, e.g. fully automated and requiring minimal manual operations that can lead to contaminations and/or false analysis caused by inaccurate handlings. It is a further advantage that minimal sample preparation may be required before introducing a specimen in a device according to embodiments of the present invention. For example, a device according to embodiments of the present invention may even work directly on whole blood or on diluted whole blood.

It is an advantage of embodiments of the present invention that a compact device is provided. For example, compared to existing FACS systems, a system according to embodiments of the present invention may be compact and may consist of few expensive components, such that this system may be used in situations where ordinary FACS systems would be too big and/or too expensive, e.g. in point of care applications and/or bioprocess monitoring applications.

It is an advantage of embodiments of the present invention that a reliable method and system may be provided, e.g. less vulnerable to fouling, calibration issues and/or drift over time, for example compared to biomass analyzers or cell sensors known in the art. Moreover, multiple channels may be used to add redundancy to the system and improve the reliability of inline monitoring.

It is an advantage of embodiments of the present invention that methods and devices are provided that are compatible with several downstream analysis methods, such as high resolution imaging of selected cells, and analysis of genomic, proteomic and metabolomic content of the selected cells. For example, gentle handling of cells to be sorted may be provided such that cells remain viable after sorting, and the genomic, proteomic and metabolomic content of cells remains unchanged during the sorting.

In a first aspect, the present invention relates to a device to analyze cells in-flow, which may comprise a fluid handling unit for the fluid handling of the biological specimen containing cells to be sorted, the fluid handling unit containing an inlet and allowing multiple flows of cells across an image recording system; a holographic imaging unit for digital imaging of the flowing specimen to be analyzed, the holographic imaging unit comprising a light source and an image sensor; a digital signal processing unit for real-time parallel image processing of recorded images of flows of cells.

In embodiments of the present invention, the fluidic handling system may comprise a plurality of microfluidic channels or streams wherein each channel or stream comprises an imaging region.

In embodiments of the present invention, the device may further comprise a focusing unit to concentrate cells in the centre of the fluid stream as they pass the imaging region. Such focusing unit may for example be based on acoustic focusing, hydrodynamic focusing, dielectrophoretic focusing or other physical principles. The objects to be sorted may for example be focused along a central axis of the microfluidic channel. The dimensions of the microfluidic channel may for example be less than 10 times the average size of the objects, e.g. preferably less than 5 times the average size of the objects to be sorted. For example, the microfluidic channel may be dimensioned to twice the size of the objects to be sorted, in order to provide a serial flow of the objects through the microfluidic channel substantially along a central axis thereof.

In embodiments of the present invention, the device may further comprise a polarizer which is added to the source and detector in order to filter polarization sensitive features.

In embodiments of the present invention, the outlet of the fluid handling system may be arranged to spot cells on carriers used in subsequent analysis such as 2D substrates (microslides) or microwell plates for further analysis.

In embodiments of the present invention, the light source may be a partially or fully coherent pulsed light source.

In embodiments of the present invention, the light source may be a Light Emitting Diode (LED) in combination with a pinhole or a laser illuminating the specimen in flow.

In embodiments of the present invention, multiple light sources may illuminate the specimen in flow from different angles.

In embodiments of the present invention, the image sensor may be a CMOS or CCD based imager arranged for recording the holographic image.

In embodiments of the present invention, the device may further comprise a decision algorithm on chip to decide which images are to be processed further.

In embodiments of the present invention, the image sensor may have dedicated pixel arrays per fluidic channel and multiple channels may have their own pixel arrays, which form a part of the image sensor.

In embodiments of the present invention, the digital signal processing unit may be a GPU (Graphics Processing Unit), an FPGA (Field Programmable Gate Array) or an ASIC (Application Specific Integrated Circuit) or another processor that is capable of processing the digital holograms at the speed of the cells in-flow.

In a second aspect, the present invention relates to a device to analyze and sort cells in-flow. A device according to embodiments of the second aspect may comprise a fluid handling unit for the fluid handling of the biological specimen containing cells to be sorted, the fluid handling unit containing an inlet and allowing multiple flows of cells across the image recording system; a holographic imaging unit for digital imaging of the flowing specimen to be sorted, the holographic imaging unit containing a light source and an image sensor; a digital signal processing unit for real time parallel image processing and for classifying (sorting algorithm) recorded images of flows of cells; a sorting unit to steer the cells to different system outlets dependent on the classifying information of the digital signal processor.

In embodiments of the present invention, the sorting unit may comprise micro-fluidic switches or nozzles that deflect the cells of interest to different outlets.

In embodiments of the present invention, the driving circuit for the switches or nozzles may be based on thermally or piezo-electrically driven actuation.

In embodiments of the present invention, the sorting unit may comprise micro-fluidic switches that deflect a liquid plug containing the cell of interest directly.

In embodiments of the present invention, the deflection may be performed by the piezoelectric deformation of a small membrane that pushes the liquid sideways.

In embodiments of the present invention, the sorting unit may comprise micro-heaters wherein the rapid heating of a liquid caused by an electrical pulse generates vapour bubbles as pressure source to displace a fluid.

In embodiments of the present invention, a trapped system may be used to perform sorting on different characteristics of the cells.

In a third aspect, the present invention relates to a method to analyze cells in-flow. The method may make use of a device as described with respect to the first aspect. A method according to embodiments of the third aspect may comprise providing a homogeneously diluted fluid comprising a heterogeneous mix of cells in a fluid handling unit comprising micro-fluidic channels; performing an illumination by means of a light source when cells pass through the micro-fluidic channels; recording the scattered light response of the cells by means of an image sensor; downloading the scattered light responses to a digital signal processing unit; and analyzing the scattered light response by means of the digital signal processing unit.

In embodiments of the present invention, the steps of recording, downloading and analysis of the scattered light responses of the cells may be done in parallel for a plurality of micro-fluidic channels.

In embodiments of the present invention, the light source may be pulsed in order to illuminate the moving cells and to take stroboscopic images.

In embodiments of the present invention, the method may further comprise an extra analysis step before downloading the recorded scattered light responses to the image sensor, wherein the result of the analysis step is a signal used in deciding which scattered light responses are analyzed by the signal processing unit.

In a fourth aspect, the present invention relates to a method to analyze and sort cells in-flow. A method according to embodiments of the present invention may make use of a device described in embodiments of the second aspect. A method according to embodiments of the present invention may comprise: providing a homogeneously diluted fluid comprising a heterogeneous mix of cells in the fluid handling unit; performing an illumination by means of a light source when cells pass through the micro-fluidic channels; recording the scattered light response of the cells with an image sensor; downloading the scattered light responses to a digital signal processing unit; classifying (sorting algorithm) and analyzing the scattered light response with the digital signal processing unit; sorting the cells based on the classification results of the signal processing unit.

In embodiments of the present invention, the classifying of scattered light responses may use a pre-stored library of holograms of interesting cells to classify cells based on a simple comparison of the recorded diffraction pattern with the pre-stored library.

In embodiments of the present invention, the classifying of scattered light responses may use different recorded cell images which are auto-correlated to each other, thereby identifying differences between cells. As an additional advantage, no prior information is needed.

In embodiments of the present invention, the classifying of scattered light responses may perform a full digital reconstruction of the hologram.

In embodiments of the present invention, the method may further comprise a downstream analysis of subpopulations of the original bio-specimen wherein the high content cell sorter system may be used as a sample preparation step for the further downstream analysis, the downstream analysis comprising high resolution imaging, molecular characterization techniques and 'omics' or sequencing technologies to reveal the genome or proteome information of the selected cells.

In embodiments of the present invention, the device may also be used not only to analyze or sort cells but also to analyze (or image) and sort objects where object shape and/or diffraction pattern are important for discrimination of subpopulations, such as sorting of crystals, e.g. protein crystals that can be formed in microfluidic systems, sorting of nanoparticles e.g. a polydisperse particle sample, sorting of nanoparticles which are part of nanoparticle assay.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
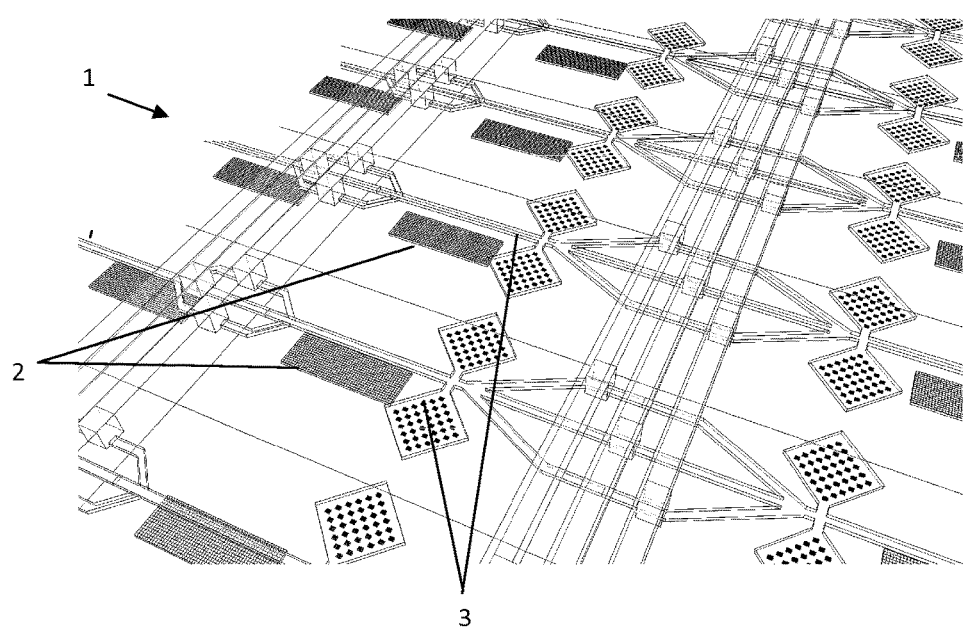
FIG. 1 shows a device for sorting according to embodiments of the present invention.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from the disclosure of the present invention, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in the description of embodiments of the present invention is referred to real-time processing, reference is made to a processing step, e.g. a method step which may typically be executed on a processing unit, that is subject to a real-time constraint, e.g. an operational time deadline for producing the result of the processing step. For example, when reference is made to real-time characterization of a holographic diffraction image, a characterization is to be established before a specific point in time, such as the time at which an object to be sorted has moved through a microfluidic channel from an imaging region to a microfluidic switch, such that this switch may be actuated in time in order to steer the object in an intended direction determined by the result of the characterization.

In a first aspect, embodiments of the present invention relate to a device for sorting objects immersed in a flowing medium. Such device comprises a holographic imaging unit, which comprises a plurality of holographic imaging elements for providing a plurality of holographic diffraction images. The device further comprises a fluid handling unit, which comprises a plurality of microfluidic channels. Each microfluidic channel comprises an imaging region for conducting the flowing medium along a corresponding holographic imaging element for imaging moving objects in the flowing medium, e.g. for imaging fast moving objects in the medium. Each microfluidic channel also comprises a microfluidic switch arranged downstream of the imaging region for controllably directing each object in the flowing medium into a selected outlet of a plurality of outlets. The device also comprises a processing unit adapted for real-time characterization of the holographic diffraction image obtained for each of the objects when passing through any of the imaging regions, in which this characterization takes into account at least one predetermined object type signature. The processing unit is furthermore adapted for controlling the microfluidic switch downstream of this imaging region in response to this characterization. Advantageously, the device for sorting objects immersed in a flowing medium may also comprise synchronization means for generating a synchronization signal, e.g. a trigger signal, representative of detected presence of each object in the flowing medium upstream of each of the imaging regions. The processing unit may be arranged for performing the real-time characterization in response to this synchronization signal, e.g. the processing unit may be adapted for performing the real-time characterization in response to this synchronization signal.

Figure 2:
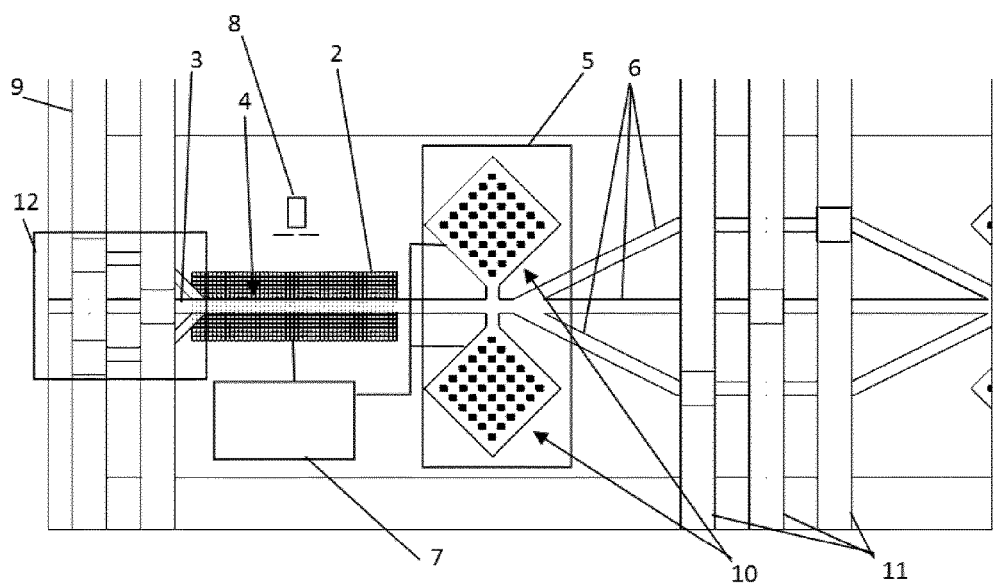
FIG. 2 shows a detail view of part of a device according to embodiments of the present invention.
Figure 5:
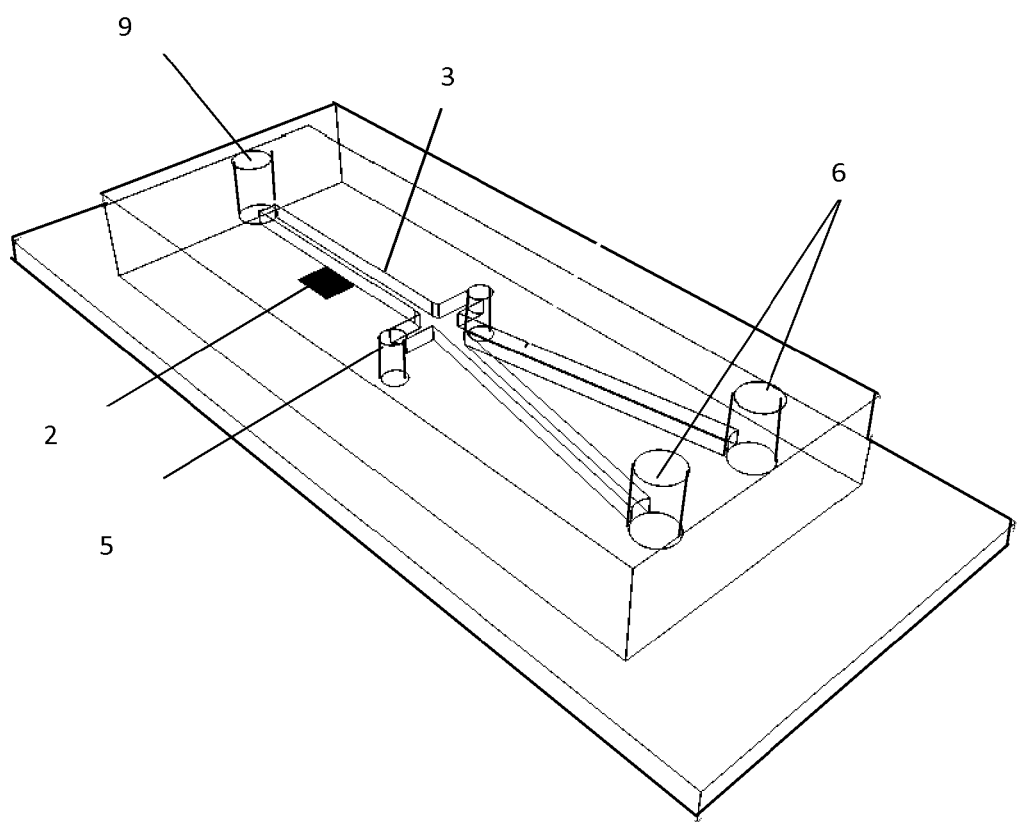
FIG. 5 shows another detail view of part of a device according to embodiments of the present invention.

Referring to the schematic overview in FIG. 1 and the detail views in FIG. 2 and FIG. 5, a device 1 according to embodiments of the present invention is shown. This device 1 is adapted for sorting objects, such as biological cells to be sorted, immersed in a flowing medium, e.g. a biological specimen. These objects may for example comprise objects of at least two types, e.g. white blood cells and red blood cells, which may be differentiated based on dimensional and/or morphological characteristics. Such device may determine one or more characteristics from the moving objects, such as cells, based on lens-free images and high speed image processing. For example, sorting of the objects under investigation may be based on classification of the objects according to characteristics calculated from lens-free holographic images. The device may sort objects, e.g. cells, at high speed based on holographic images processed in real time.

The device 1 comprises a holographic imaging unit, which comprises a plurality of holographic imaging elements 2 for providing a plurality of holographic diffraction images. The holographic imaging unit may comprise an image sensor, e.g. a CMOS or CCD image sensor. For example, the holographic imaging unit may comprise a CMOS image sensor partitioned into the holographic imaging elements 2, each holographic imaging element 2 for example comprising an array of CMOS image pixels, for example a 6×6 pixel array, or a 128×128 pixel array, embodiments of the present invention however not being limited to these dimensions. The CMOS or CCD image sensor may for example be adapted for recording holographic diffraction images of single objects passing through the microfluidic channel, for example at high capturing rates, e.g. at more than 1000 frames per second, e.g. 2000 frames per second or more.

Thus, the image sensor may be a CMOS or CCD based imager arranged for recording the holographic image. An active pixel area on the image sensor may be used to record the images of the objects, e.g. cells, flowing through the fluid handling unit. The active pixel area may be defined as the sensor area which records scattered light responses of cells, e.g. while the cells are passing the imaging region 4 of the micro-fluidic channels 3. The pixel array may be positioned at a predetermined distance from the microfluidic channels 3. The pixel array may in one example form part of a chip, e.g. a semiconductor chip such as a silicon chip. Such a chip can also comprise other functionalities, e.g. in an integrated manner, as for example indicated in FIG. 3. In one example, the chip is positioned in a plane and the microfluida are positioned in a plane, whereby the two planes do not coincide. The image sensor may be divided in active pixel arrays, each pixel array being related to an imaging region 4 of each microfluidic channel 3. The image sensor may furthermore be adapted for parallel readout of the pixel arrays, e.g. such that holographic diffraction images may be provided by the holographic imaging elements 2 simultaneously and independently from each other. The image sensor may comprise read-out circuitry for parallel readout of pixel arrays whereby each pixel array can be read out individually. The processing unit 7 may hence process holographic images provided by different pixel arrays substantially parallel. In one example, the image sensor is selected so as to have a pixel size as small as possible for obtaining a high resolution, so as to have a read out that is as quick as possible with a number of bits per pixel as high as possible. The image sensor may be selected to have an appropriate combination of the above mentioned properties.

In embodiments of the present invention, the imaging region 4 may be arranged at an angle, e.g. an angle in the range of 1° and 44°, e.g. an angle in the range of 5° and 30°, of an angle in the range of 10° and 20°, with respect to the grid alignment of the CMOS or CCD image sensor. In such embodiments, the processing unit 7 may be furthermore adapted for constructing a super-resolution holographic diffraction image from a plurality of holographic diffraction images obtained for each of the objects in flow. Methods are known in the art to obtain such super-resolution images, e.g. images having a spatial resolution double of the single-image resolution obtainable by the CMOS or CCD image sensor, by combining information in multiple images relating to the same object subject to a translation. The angle between the image sensor grid alignment and the imaging region of the microfluidic channel may induce a shift of the object in flow as imaged in one image with respect to another image, e.g. a subsequently captured image, such that this shift has non-zero components along all imaging grid axes.

In embodiments of the present invention, the device 1 may comprise synchronization means for generating a synchronization signal, e.g. a trigger signal, representative of detected presence of each object in the flowing medium upstream of each of the imaging regions 4 and/or representative of detected presence of each object in the flowing medium upstream of the microfluidic switch 5. The processing unit 7 may be arranged for performing the real-time characterization in response to said synchronization signal, e.g. in response to the detected presence upstream of each of the imaging regions 4. This synchronization means may comprise a photodetector for receiving light modulated by the object, e.g. light reflected by the object or light transmitted through the object. For example, such photodetector may generate the synchronization signal in response to a detected light intensity which is modulated, e.g. decreased, when the object passes through the microfluidic channel. The synchronization means may comprise, alternatively or additionally, at least one electrode for detecting an electrical signal affected by said object, for example, for detecting a change in impedance when the object passes through the microfluidic channel. Furthermore, the synchronization means may be incorporated in the holographic imaging elements, for example, the synchronization means may comprise pixel elements in the holographic imaging elements, e.g. a pixel element in each holographic imaging element which is located at the upstream end of the corresponding imaging region. The synchronization means may also be incorporated in the microfluidic channels 3, e.g. may comprise at least one electrode arranged in the microfluidic channel wall.

It is an advantage of these synchronization means that a simple and computationally efficient detection may be performed in order to reduce the computational workload of a processing unit 7 for classifying objects in fluid suspension.

These synchronization means may also comprise at least one flow monitoring device for providing information relating to the velocity and/or acceleration of the object when the presence of this object is detected. For example, a flow measurement may be performed in the microfluidic channel or a pump phase detection may be performed in order to provide additional information from which the time of arrival of the object in the imaging region and/or in the microfluidic switch may be predicted. Thus, changes in flow velocity, e.g. caused by time-dependent pump efficiency, may be taken into account for accurate synchronization of the imaging and sorting of each object.

In embodiments of the present invention, the holographic imaging elements 2 may be adapted for receiving the synchronization signal from the synchronization means. For example, in embodiments of the present invention, the holographic imaging elements 2 may be adapted for detecting the presence of an object in the flowing medium and for providing holographic diffraction image data in response to such detection. thus, integrated circuitry on a CMOS image sensor may detect the presence of an object in the field of view of a holographic imaging element by repeatedly evaluating a detection criterion, e.g. evaluating the synchronization signal, for example evaluating an image intensity threshold, and transmit the image data obtained from the holographic imaging element to the processing unit 7 when such criterion is satisfied. It is an advantage of such embodiments that a simple and computationally efficient detection may be performed locally in order to reduce the computational workload of a processing unit 7 for classifying objects in fluid suspension.

For example, a decision algorithm may be implemented on the holographic imaging unit, e.g. on the imager chip, to decide which images are to be processed further by the processing unit 7, e.g. by a digital processing unit such as a computer system or dedicated integrated circuit device. Since some images do not contain a cell response, e.g. when a cell is not present in the imaging region 4 when a recording is performed, they are not useful for handling and a direct decision mechanism to discard those images may considerably speed up the imaging and sorting.

In a device 1 according to embodiments of the first aspect of present invention, each of the plurality of microfluidic channels may further comprise a meandering segment arranged between the imaging region 4 and the microfluidic switch 5 for delaying the transition of each of the objects from the imaging region 4 to the microfluidic switch 5 while the real-time characterization is performed. Thus, a processing time overhead may be taken into account, such that the microfluidic switch 5 may be controlled in time in accordance with the characterization of the object to be sorted.

The holographic imaging unit may further comprise at least one at least partially coherent pulsed light source 8 for illuminating the flowing medium. This at least one at least partially coherent pulsed light source 8 may comprise a laser. Alternatively, this at least one at least partially coherent pulsed light source 8 may comprise a Light Emitting Diode (LED) or laser source, such as a laser diode, optically coupled to a pinhole. For example, each of the plurality of holographic imaging elements may have a corresponding light source 8, such that light emitted by this light source interacts with an object to be sorted when present in a corresponding imaging region of a microfluidic channel. Interference between the light after interaction with such object (object beam) and a reference portion of the light emitted by the light source (reference beam), e.g. a portion which has propagated past the object without having interacted therewith, may cause a holographic interference pattern to form on the imaging plane of the holographic imaging element 2. From this interference pattern, according to embodiments of the present invention information may be gained about the object, e.g. a classification of such object in predetermined types.

Although the least one at least partially coherent pulsed light source 8 may be substantially monochromatic, the at least one at least partially coherent pulsed light source 8 may also comprise a multi-wavelength at least partially coherent pulsed light source, for example may emit at least partially coherent light of two or more wavelengths, e.g. at four wavelengths. Thus, the partially coherent light sources may comprise light sources with one or multiple wavelengths, e.g. multiple discrete wavelengths.

The at least one at least partially coherent pulsed light source 8 may also comprise a plurality of light sources, e.g. laser diodes or light emitting diodes, configured for illuminating the flowing medium from different angles. Such a plurality of light sources may improve the 3D information contained in the diffraction pattern.

Furthermore, the holographic imaging unit may also comprise at least one polarizer optically coupled to the light source and image sensor for selecting a polarization of light. Such polarizer may be added to the light source and image sensor in order to filter polarization sensitive features.

In embodiments, the at least one at least partially coherent pulsed light source 8 may be arranged in a lens-less imaging configuration. A pinhole aperture may be arranged on the microfluidic channel for collimating the light emitted by the at least partially coherent pulsed light source 8. The at least one at least partially coherent pulsed light source may comprise a pinhole arranged on each microfluidic channel, e.g. a transparent pinhole window provided in the microfluidic channel wall. It is an advantage of a lens-less imaging configuration that high-density integration, e.g. parallelization of many microfluidic channels on a single compact device, may be achieved. It is an advantage of the pinhole aperture arrangement that a substantially point-like light source may be achieved which illuminates the objects in flow from a short distance, e.g. a spatial light distribution similar to a point-like source emitting from the wall of the microfluidic channel may be achieved. A short distance between such point-like source and the objects being imaged is particularly advantageous since a large point zoom factor may be achieved. By using such a point-like source, e.g. located in the range of 40 μm to 400 μm from the object and located in the range of 1 mm to 10 mm, e.g. in the range of 2 mm to 5 mm, from the imager, the angle between the scattered light and the reference beam is reduced. This way the same scatter pattern may result in an interference pattern with much wider fringes for the point-like source compared to light which forms substantially planar wavefronts. Because of this, more information may be recorded, e.g. the fringe pattern provides more information about the light scattering object. Advantageously, a zoom effect, e.g. having a zoom factor in the range of 10 to 25, may be thus obtained.

Figure 7:
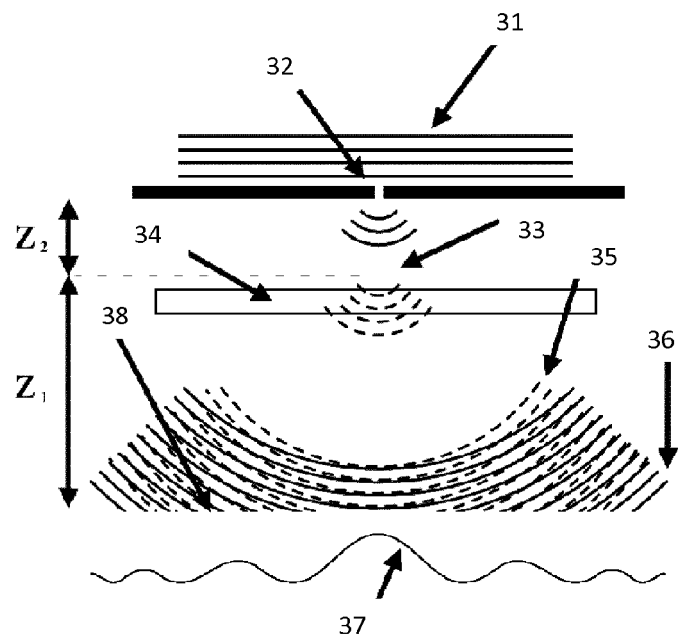
FIG. 7 shows a pinhole in a device according to embodiments of the present invention.

FIG. 7 illustrates such pinhole arrangement. A substantially planar wavefront 31, e.g. monochromatic light from a collimated beam or from a pinhole far away, may be collimated by the pinhole 32, which may be arranged at a distance $Z_2$ from the imaged object 33, e.g. at a distance $Z_2$ from the central axis of the microfluidic channel along which the objects in flow in the medium 34 are focused. The light collimated by the pinhole 32 can then interact with the object 33 and may impinge on the imager, which is arranged at a distance $Z_1$ from the object 33, e.g. at a distance $Z_1$ from the central axis of the microfluidic channel. The light 35 scattered by the object may then interact with the transmitted light 36 which serves as reference beam, e.g. the light which transmits substantially unmodulated through the medium 34, to form an interference pattern 38 on the imager 37. When the object and the pinhole are in alignment the fringe on the camera under the pinhole typically may have a broader shape and higher intensity than fringes which are further away. Therefore, the imager may have an adapted pixel configuration, e.g. which could have a lower spatial resolution at the position of the imager which is aligned with the pinhole, and a higher spatial resolution on the edge of the imager. Such pixel arrangement is shown in FIG. 7 by the pixel elements of the imager 37, illustrated as boxes. Furthermore, since the intensity of the fringe patterns is lower at further distances from the centre, the imager may be designed in such a way that those pixels are more sensitive. This way, the full quantization scale of the pixels could be used both for the inner as the outer fringes.

Figure 8:
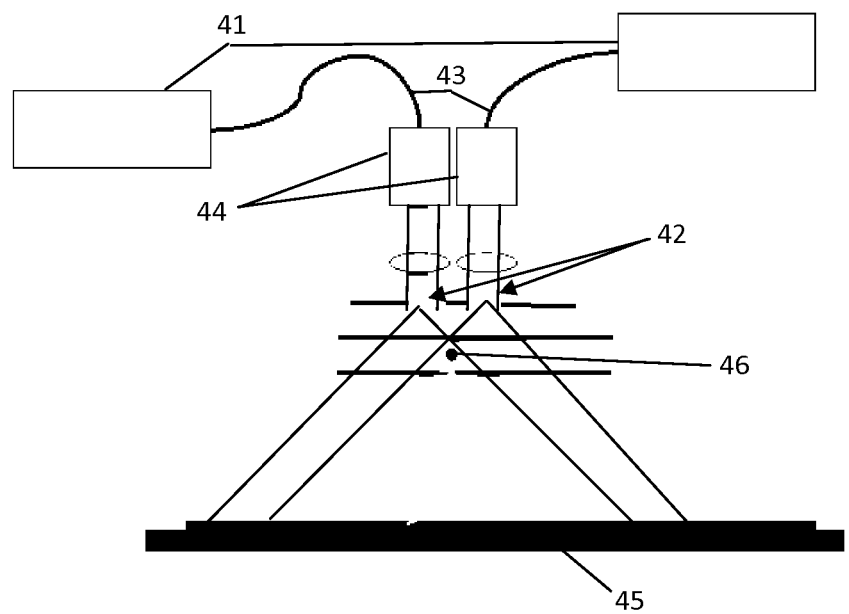
FIG. 8 shows a first exemplary arrangement of light source and imaging detector according to embodiments of the present invention.

Referring to FIG. 8, a exemplary arrangement for two at least partially coherent light sources is shown. Two light emitters 41, e.g. lasers, are optically coupled to two pinholes 42, e.g. through optic fibers 43 and fiber collimators 44. Furthermore, the imager 45 may be provided with a checkerboard filter, such that pixels are tuned to alternatingly the first light emitter and the second light emitter. This way, two side-ways illuminated holograms of the object 46 may be acquired simultaneously.

Figure 9:
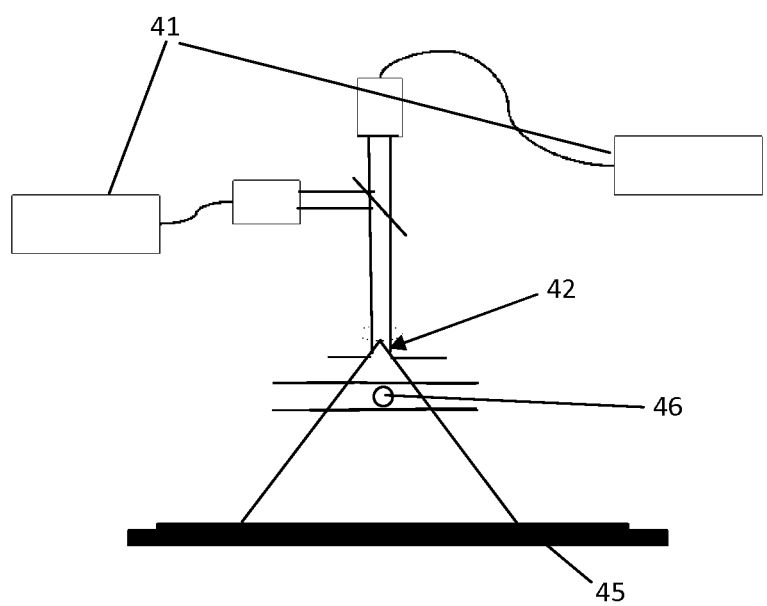
FIG. 9 shows a second exemplary arrangement of light source and imaging detector according to embodiments of the present invention.

In FIG. 9, another exemplary arrangement for two at least partially coherent light sources is shown. Two light emitters 41, e.g. lasers, are optically coupled to one pinhole 42. Here, the imager 45 may also be provided with a checkerboard filter, such that pixels are tuned to alternatingly the first light emitter and the second light emitter. This way, two holograms of the object 46 may be acquired simultaneously corresponding to different reference beam wavelengths.

Figure 10:
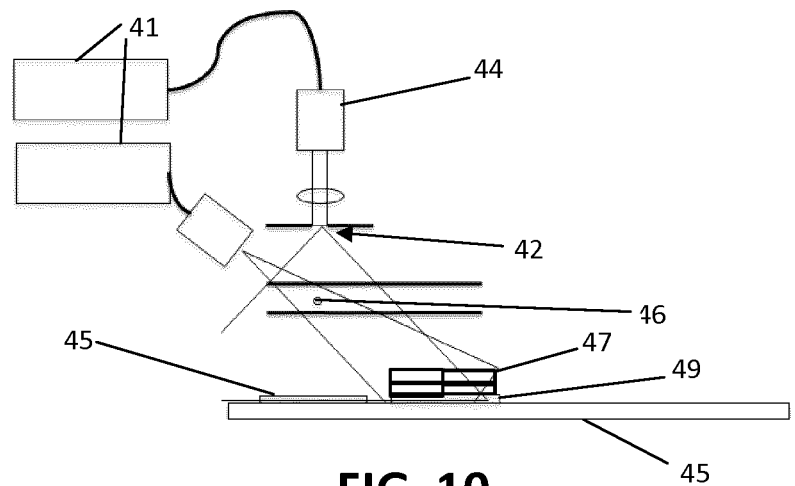
FIG. 10 shows a third exemplary arrangement of light source and imaging detector according to embodiments of the present invention.

In FIG. 10, a third exemplary arrangement for two at least partially coherent light sources is shown. One of the light emitters 41, e.g. lasers, is optically coupled to one pinhole 42, while the other light emitter is only collimated by the fiber collimator 44. Here, the imager 45 comprises a holographic imaging portion 48 and a fluorescence imaging portion 49, in which the fluorescence imaging portion is provided with a hyperspectral filter 47 in order to obtain signals corresponding to different fluorescence wavelengths by corresponding pixels.

Figure 11:
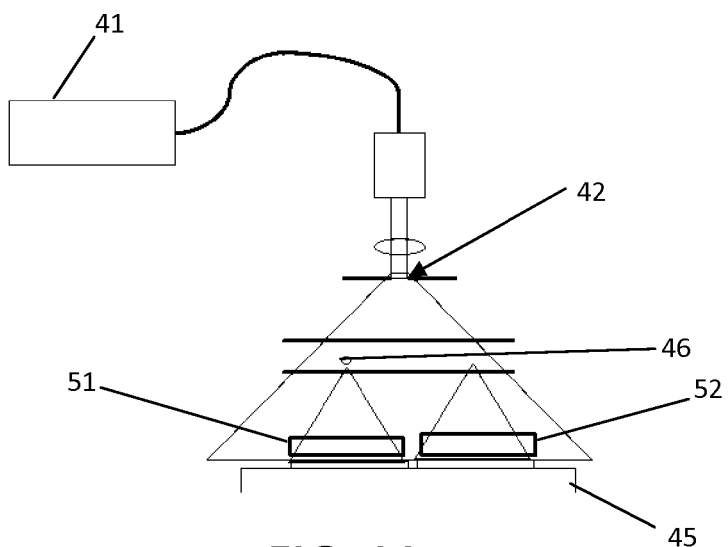
FIG. 11 shows a fourth arrangement of light source and imaging detector according to embodiments of the present invention.
Figure 12:
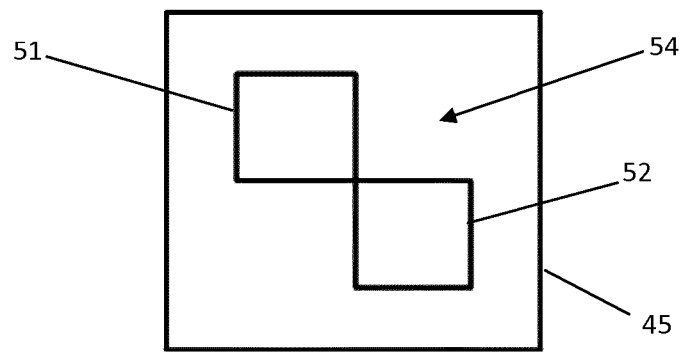
FIG. 12 shows an imager and spectral filter layout for the fourth exemplary arrangement of light source and imaging detector according to embodiments of the present invention.

A fourth exemplary arrangement for one at least partially coherent light source is shown in FIG. 11. Here, a pinhole 42 provides a wide field of illumination, such that the object 46 will be imaged by a first imaging portion and a second imaging portion of the imager 45 while moving along the microfluidic channel. These portions are fitted two corresponding spectral filters 51, 52, such that each imaging portion may obtain an image corresponding to a different fluorescence wavelength. Furthermore, as shown in FIG. 12, by leaving portions of the imager uncovered by these different spectral filters 51, 52, a holographic diffraction image may be obtained by the area 54 of the imager 45 which remains uncovered.

According to an embodiment of the invention, the imager is a snap-shot hyperspectral imager wherein the imager comprises at least two spectral filters (e.g. a tiled layout). As an advantage of embodiments of the invention, different spectral data can be captured by obtaining a single image, thus increasing throughput of the cell sorting.

Figure 3:
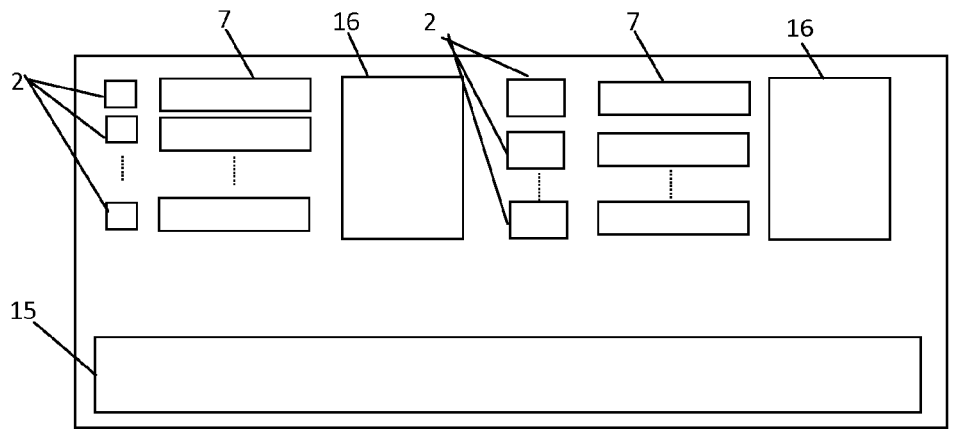
FIG. 3 shows an example design of a CMOS backplane for use in a device according to embodiments of the present invention.

To make a high-resolution image of an large area we propose making an array of closely spaced pinholes which can be driven separately by optical fibers above the pinholes. This type of set-up is shown in FIG. 3.

In embodiments of the present invention, the device 1 may furthermore comprise a plurality of fluorescence imaging elements for providing a plurality of fluorescence images. The imaging regions 4 may furthermore be adapted for conducting flowing medium along a corresponding fluorescence imaging element of this plurality of fluorescence imaging elements. For example, the holographic imaging element and the fluorescence imaging element which both correspond to an imaging region 4 may be integrated on the same CMOS or CCD image sensor or may be both integrated on the same CMOS or CCD image sensor region. The processing unit 7 may be adapted for real-time characterization of the holographic diffraction image and fluorescence image obtained for each of the objects when passing through said imaging regions 4. For example, a characterization of the imaged object may be performed taking both diffraction image and fluorescence image information into account, e.g. in order to advantageously obtain a classification of the object with high specificity.

For example, the imaging region 4 may be divided into two imaging zones along the flow direction in the microfluidic channel, in which an object is subjected in the first zone to holographic diffraction imaging and in the second zone to fluorescence imaging, or vice versa, in the first zone to fluorescence imaging and in the second zone to holographic diffraction imaging. The fluorescence imaging may be limited to detecting a single fluorescence signature, but may also comprise a multi-spectral or hyper-spectral fluorescence detection. Each of the plurality of fluorescence imaging elements may comprise a multi-spectral filter assembly. For example, each fluorescence imaging element may comprise a plurality of imaging pixels, in which at least one first imaging pixel is provided with a first wavelength filter and at least one second imaging pixel is provided with a second wavelength filter, such that the at least one first imaging pixel and the at least one second imaging pixel are adapted for detecting fluorescence signals emitted in different wavelength ranges. Each of the plurality of fluorescence imaging elements may be used to provide a plurality of fluorescence sensing signals for each of said objects when passing through said imaging regions, e.g. each fluorescence sensing signal corresponding to a different wavelength ranges.

While fluorescence imaging and holographic diffraction imaging may be combined for improved classification of an object in an imaging region of a microfluidic channel, e.g. a single-stage sort may be based on both holographic diffraction imaging and fluorescence imaging, in a cascade arrangement, e.g. where in a first microfluidic channel objects are sorted according to a first criterion and in a second microfluidic channel a subset of objects already sorted according to this first criterion are further sorted according to a second criterion, a first stage of the cascade may implement a sort based on holographic diffraction imaging and a further stage of the cascade may implement a sort based on fluorescence imaging.

The device further comprises a fluid handling unit, which comprises a plurality of microfluidic channels 3. In embodiments of the present invention, the fluid handling unit may also comprise an inlet 9 for distributing the flowing medium over at least two of this plurality of microfluidic channels 3, and preferably over a large number of these microfluidic channels. For example, an inlet 9 may distribute the flowing medium over more than 10 parallel microfluidic channels, for example over 20 or more parallel microfluidic channels, or even more preferred, over more than 100 parallel microfluidic channels, for example over 1.000 parallel microfluidic channels. This plurality of microfluidic channels 3 may be integrated in a single integrated microfluidics device, e.g. on a single chip, such that a large number of objects in fluid suspension may be sorted in parallel by a device 1 according to embodiments of a second aspect of the present invention, while such device 1 remains compact and easy to produce by standard microfluidic chip design methods known in the art. For example, in an embodiment of the present invention, the image sensor may have dedicated pixel arrays per microfluidic channel 3 and multiple channels may have their own pixel arrays, which form a part of the image sensor.

In an embodiment of the present invention, the holographic imaging unit, e.g. the image sensor, may be exposed to different scattered light responses coming from different microfluidic channels 3 on different holographic imaging elements 2, e.g. pixel arrays of the image sensor. The image sensor may be arranged such that blocks of pixels are allocated to image a flow of cells and multiple blocks can image multiple flows of cells in parallel. In an embodiment of the present invention, a typical pixel array may have 64×64 or 128×128 pixels. Depending on the required resolution of the holographic diffraction patterns, e.g. holograms, this array can be larger or smaller.

Said plurality of microfluidic channels 3 may also be arranged in a cascade, for example as shown in the schematic overview in FIG. 1, such that at least one outlet 6 of at least one first microfluidic channel 3 feeds the flowing medium into at least one second microfluidic channel 3. For example, a cascaded fluid handling unit may comprise a first sorting stage, for example comprising 1000 parallel microfluidic channels, in order to perform a rough sorting (e.g. red blood cells from white blood cells, or lymphocytes from other white blood cells), and a second sorting stage, for example comprising 20 microfluidic channels, in order to perform a further differentiation. A rough sorting may for example sort out red blood cells from a blood sample and feed other cells into the second sorting stage, which, for example, sorts out white blood cells and/or circulating tumour cells (CTC).

In an example embodiment, in the case of classifying very rare cells, a cascade system may be used in which a first rough sorting is made based on one property and a second, third etc. imaging and sorting event may refine the sorting upon other properties. In an embodiment of the second aspect of the present invention, a first system may comprise many, e.g. 1.000, channels that roughly sort white blood cells from red blood cells, based on information which can be achieved very quickly such as total integrated intensity on the pixel array or even the intensity recorded by a single pixel photodetector, which can be compared with a threshold value. The second trap may comprise fewer channels that discriminate different subtypes of white blood cells and even can get out very rare cells such as circulating cancer cells or stem cells.

In an embodiment of the first or second aspect of the present invention, the fluid handling unit may comprise a plurality of microfluidic channels 3, each allowing large number of cells to flow pass the corresponding holographic imaging elements 2.

Each microfluidic channel may comprise an imaging region 4 for conducting the flowing medium along a corresponding holographic imaging element for imaging objects in the flowing medium. Therefore, the fluid handling unit may allow multiple flows of objects, e.g. cells, across the holographic imaging unit, e.g. an image recording system.

Each such channel 3 may comprise an imaging region 4 where imaging of the objects in flow, e.g. cells, may be performed such that imaging data may be subsequently sent to the processing unit 7.

Each microfluidic channel 3 may also comprise a microfluidic switch 5 arranged downstream of the imaging region 4 for controllably directing each object in the flowing medium into a selected outlet of a plurality of outlets 6, e.g. to steer the objects, e.g. cells, to different system outlets according to classifying information provided by the processing unit 7, e.g. the digital signal processor. The microfluidic switches 5 may deflect objects, e.g. the cells of interest, to different outlets, in which the driving circuit for the switch to steer the objects may be based on any suitable technique, such as for example thermally or piezo-electrically driven actuation.

Droplet based switches are known in the art for different purposes including inkjet printer heads. Such switch may be optimized to be fast enough for the purpose of fluidic sorting, for example, for a specific application in biological cell sorting, to allow at least 1.000 and close to 20.000 cells to be sorted per second. Today's state of the art printer heads allow to form, steer and print up to 30.000 droplets per second per nozzle, but the boundary conditions in terms of maximum applicable actuation forces for actuation droplets versus cells are different because of the mechanical forces being experienced by cells that have to remain viable during the switch. The success of cell printing using commercial printers has motivated several research groups to initiate cell printing techniques. The actuation of droplets needs to be synchronized with the cells flowing so that each droplet contains the cell to be sorted and gets steered to the right outlet.

The microfluidic switches 5 may comprise thermally or piezo-electrically driven flow deflection means. For example, the microfluidic switches 5 may deflect a liquid plug containing the cell of interest directly. Such microfluidic switches 5 may use the principle of piezoelectric deformation of a small membrane to push the liquid sideward so that particles or cells are moved towards another outlet. Inline micro-fluidic sorting of 3.000 cells per second has been demonstrated using this principle.

The microfluidic switches 5 may comprise a fluidic side chamber having a volume which can be adjusted by a piezoelectric or thermal actuator to change the trajectory of the object in the microfluidic channel. The microfluidic switches 5 may comprise a fluidic side chamber having a volume which can be adjusted by an externally actuated moveable membrane to change the trajectory of the object in the microfluidic channel.

The microfluidic switches 5 may comprise micro-heaters 10 for generating vapour bubbles for displacing objects in the flowing medium. Such micro-heaters may effect a rapid heating of a liquid caused by an electrical pulse to generate vapour bubbles as pressure source. It is an advantage of such approach that it may perform simple and fast microfluidic switching. A bubble may be generated in a few microseconds, e.g. as reported in Sensors and Actuators B 117 (2006) 523-529 and in Dynamics in microfluidic systems with microheaters, Technical Proceedings of the 1999 Conference on Modelling and Simulation of Microsystems. Nucleation of such a bubble and the fluid displacement caused by the pressure is fast enough to steer a plug of liquid containing a cell in a certain direction at the desired speed. This principle has been used to demonstrate successful sorting of 20 micrometer microspheres in Sensors and Actuators B 117 (2006) 523-529 and sorting of single cells in different outlet directions has been demonstrated. Also here, the actuation of the liquid formation may need to be perfectly synchronized with the cells to be sorted.

In embodiments, the microfluidic switches (5) may comprise a plurality of electrode elements electrically connected to an alternating current driving means for changing the trajectory of the object by dielectrophoresis (DEP). Such dielectrophoresis-based sorting is known in the art. For example, in DEP manipulation, an impulse moment can be imparted on an charge-neutral matter object by polarization effects in non-uniform electric fields, e.g. by moving through a alternating current potential field.

Alternatively, the microfluidic switches 5 may comprise a plurality of ultrasonic transducers for changing the trajectory of the object by acoustic radiation force.

The outlets 6 may be adapted for spotting objects on a removable carrier, such as a 2D substrate, e.g. a microslides, or a microwell plate. For example, corresponding outlets 6 of a plurality of microfluidic channels 3 arranged in parallel may be connected to output channels 11, which may feed into corresponding spraying nozzles for depositing the sorted objects onto a carrier for subsequent analysis.

In embodiments of the present invention, the microfluidic channels 3 may furthermore comprise a focusing unit 12 for concentrating the objects in a central region of the flowing medium in the imaging region 4, for example for focusing these objects in a central cross-sectional area of the flow in the imaging region. Thus, the focusing unit concentrates objects such as biological cells in the centre of the fluid stream as they pass the imaging region. It is an advantage of such focusing that image recordings may be more uniform, e.g. standardized, over multiple objects of the same type. Such focusing methods have been used in many FACS and micro-fluidic systems to improve the alignment of the cells in front of a light source, e.g. a laser, and typically improve the sensitivity and accuracy of the sorting. Such focusing unit may be based on any suitable focusing technique, such as acoustic focusing, hydrodynamic focusing, dielectrophoretic focusing or other physical principles. By way of illustration, hydrodynamic focusing is shown in the drawings, embodiments of the present invention not being limited thereto.

Figure 13:
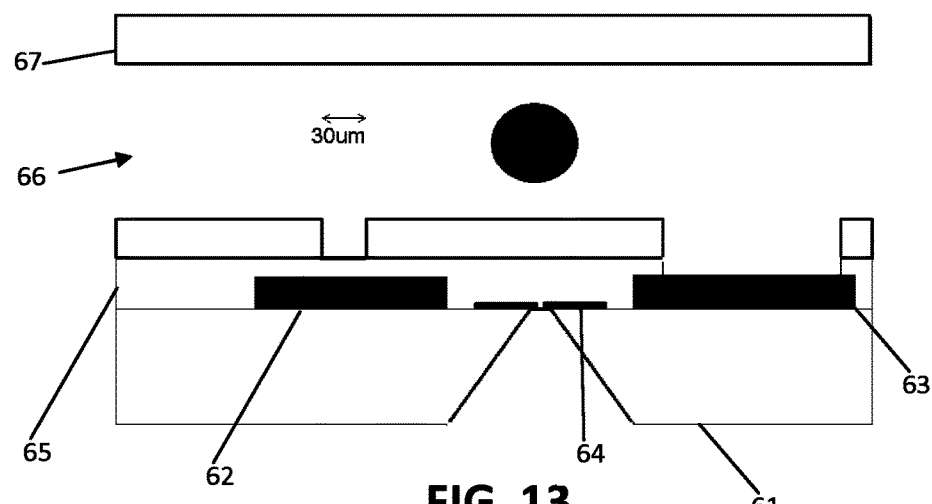
FIG. 13 shows an exemplary layered structure for a device according to embodiments of the present invention.
Figure 14:
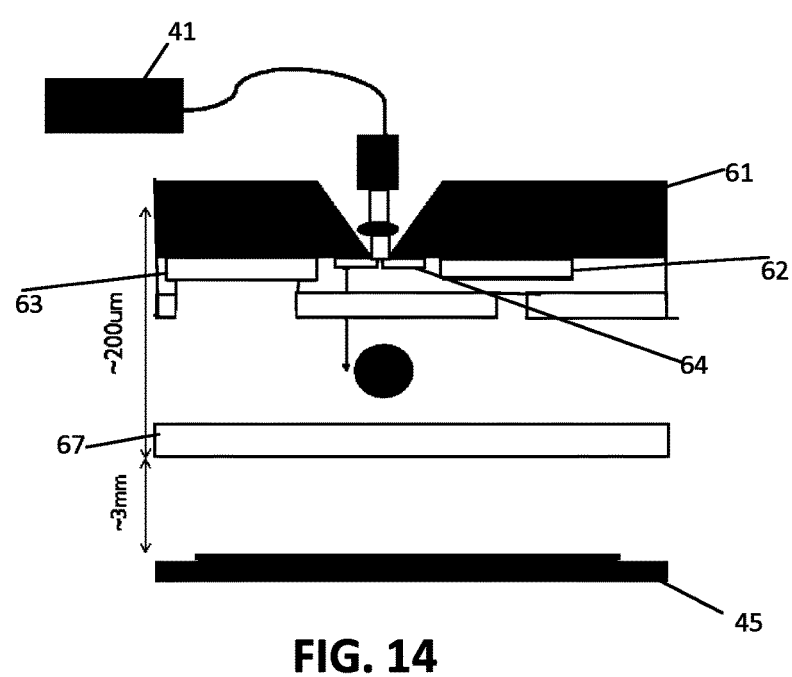
FIG. 14 illustrates the arrangement of the layered structure shown in FIG. 13 in a device according to the first aspect of the present invention.

An exemplary implementation of a device according to embodiments of the present invention is shown in FIG. 13, which may be manufactured by semiconductor processing technology. Here, on a substrate 61, e.g. a silicon substrate, a metal conductor 62 for a thermal heater, a bondpad 63, and a metal collimating element 64 for forming a pinhole are provided in a first processing pass in an insulating layer 65. In a second pass, the microfluidic channel 66 may be formed using a polymer spacer, or a combination of polymer spacer and a cover glass 67. An opening for projecting light onto the pinhole is be furthermore provided by backside etching of the silicon, e.g. a KOH backside etching process. FIG. 14 shows the semiconductor device of FIG. 13 in a device according to the first aspect of the present invention, including a light emitter 41 for coupling light into the pinhole formed by the metal collimating element 64. The image sensor 45 is arranged at a suitable distance from the wall of the microfluidic channel, e.g. from the cover glass 67.

Figure 15:
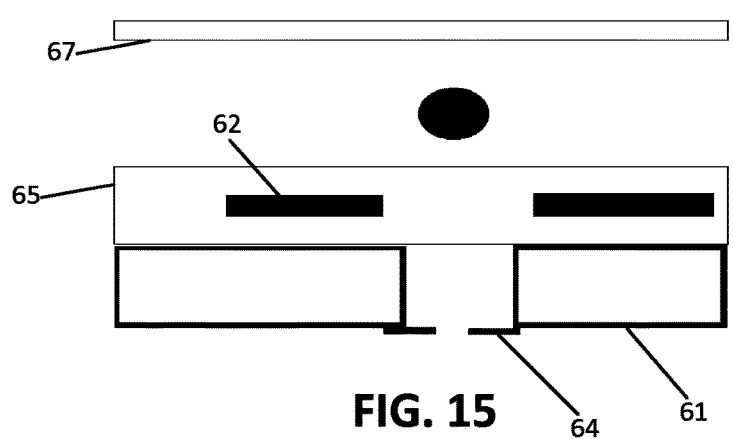
FIG. 15 shows a second exemplary layered structure for a device according to embodiments of the present invention.

FIG. 15 shows another exemplary implementation on a glass wafer substrate 61. The pinhole is formed by a collimating element 64 arranged back-side on the substrate, such that the substrate may advantageously function as a spacer element between the pinhole and the object to be imaged.

The device may also comprise a processing unit 7 adapted for real-time characterization of the holographic diffraction image obtained for each of said objects when passing through any of these imaging regions 4, in which the characterization takes into account at least one predetermined object type signature. The processing unit may furthermore be adapted for controlling the microfluidic switch downstream of this imaging region, e.g. the imaging region through which the object was moving during image acquisition, in response to this characterization. This processing unit 7 may comprise a Graphics Processing Unit, a Field Programmable Gate Array and/or an Application Specific Integrated Circuit. Micro-fluidic sorting may be provided by embodiments of the present invention based on the application of classification algorithms on digital holographic diffraction images. Depending on the outcome of the classification, cells may be steered, e.g. pushed sideward, in order to end up in a different outlet of the microfluidic channel by the microfluidic switch.

The processing unit 7, e.g. the digital signal processor, may analyze and classify holographic diffraction images, e.g. images of cells. Such classification may comprise executing a sorting algorithm based on signatures extracted from either non-reconstructed, partially or fully reconstructed digital holograms.

An example embodiment of the processing unit 7 and the holographic imaging unit integrated on a single CMOS backplane is shown in FIG. 3. This integrated implementation may comprise the plurality of holographic imaging elements 2, including the analogue front end for analogue signal conditioning of the image sensor signals, an integrated circuit element 15 for storing images, transferring images and/or communicating with an external receiver, e.g. for providing a user interface, microfluidic switch driver circuitry 16 and circuitry for providing the characterization functionality of the processing unit 7 as described hereinabove. Alternatively, a part or the entire analogue front end for analogue signal condition of the image sensor signals may also be part of the processing unit 7.

In a second aspect, the present invention relates to a method for sorting objects immersed in a fluid. Such method comprises introducing a flow of said fluid into a plurality of microfluidic channels, in which each microfluidic channel comprises an imaging region. The method further comprises the steps of recording a holographic diffraction image of each object when passing through any of said imaging regions, characterizing the holographic diffraction image obtained for each of the objects when passing through any of the imaging regions in real-time, in which this characterization takes into account at least one predetermined object type signature, and steering each object into an outlet, in which this outlet is selected from a plurality of outlets as a function of the characterization for the object.

A method according to embodiments of the present invention may further comprise a step of introducing the flow of liquid from at least one of said plurality of outlets into at least one further microfluidic channel, the or each at least one further microfluidic channel comprising a further imaging region. Such method may further comprise recording an image, e.g. holographic diffraction image or fluorescence image, of each object when passing through the or any of the further imaging regions, characterizing the image thus obtained taking into account at least one object type signature, and steering the object into a further outlet selected from a plurality of further outlets as a function of the characterization for the object.

Figure 4:
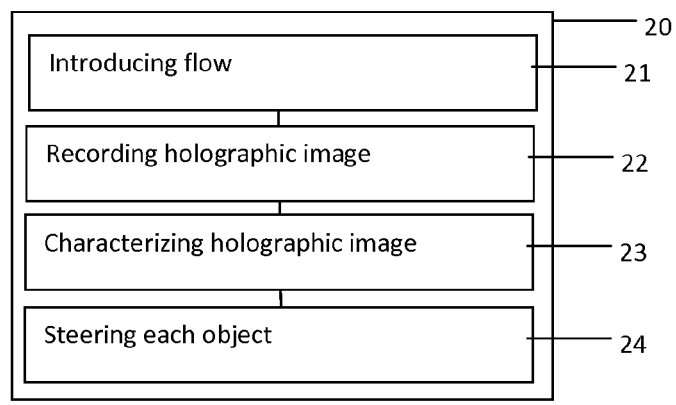
FIG. 4 schematically illustrates a flow chart of a method according to embodiments of the present invention.

An exemplary method 20 for sorting objects immersed in a fluid according to embodiments of the present invention is shown in FIG. 4. Such method may determine one or more characteristics from moving objects, such as cells, for example, using a device as described in relation to the first aspect of the present invention. It is an advantage of embodiments of the present invention that images are recorded for characterizing these objects in a very short time frame in order to keep up with the flow of the objects through micro-fluidic channels. Such method 20 may furthermore analyze and sort objects, such as cells, based on classification of the objects according to the characteristics calculated from lens-free images. The method may analyze and sort cells at high speed based on holographic images processed in real time.

In embodiments of the present invention, the method 20 comprises the step of introducing 21 a flow of said fluid into a plurality of microfluidic channels, in which each microfluidic channel comprises an imaging region. For example, a homogeneously diluted fluid comprising a heterogeneous mix of objects, for example biological cells, may be introduced in a fluid handling unit. In such fluid handling unit comprising microfluidic channels, an illumination of the cells, e.g. an illumination by a light source, may be performed when the cells pass through the imaging regions of these micro-fluidic channels. It may be advantageous that the fluid is homogeneously diluted to the extent that cells flow individually past a holographic imaging system. One possible optical configuration of a light source and sensor array may provide optical transmission through the fluid handling system, so that the source emits light that is scattered by the specimen in the fluid handling system and phase sensitive information is recorded at the other side of the fluid handling system on the image sensor. This may require the fluid handling system, e.g. particularly the imaging regions of the microfluidic channels, to be transparent for the light used.

In an embodiment, the light source, that could be at least partially coherent, may be pulsed in order to illuminate the moving objects and to take stroboscopic images. Cells may typically move in front of the imager with velocities from a few cm/s to a few m/s. The pulsed source as well as the light detection system could be configured appropriately to image objects at these velocities. For example, 100 ns light pulses may be suitable for cells moving with a velocity of 1 m/s, and 10 ns light pulses may be suitable for cells moving with a velocity of 10 m/s. In order to acquire sharp holographic diffraction images, short light pulses may be used to avoid blurring by moving cells. Adequate pulse power may be required to have enough photons at the image sensor without optothermally damaging the objects, e.g. moving cells. Stroboscopic images may be downloaded to a digital signal processing unit for analysis purposes. The reduced number of pixels for holographic stroboscopic imaging compared to ordinary imagers may present an advantage with respect to high throughput in flow imaging.

The method 20 further comprises the step of recording 22 a holographic diffraction image of each object when passing through any of said imaging region, for example, recording the scattered light response of the cells with an image sensor.

This recording 22 may comprise evaluating whether the object is passing through the imaging region, e.g. evaluating whether the object is passing through the imaging region before recording such holographic diffraction image. For example, a local decision algorithm may be executed on the imager in order to determine which images, e.g. stroboscopic images, are pushed to a digital signal processing unit for analysis. Since many images may not contain any useful information at all, e.g. when they contain no information about objects to be sorted, the local decision algorithm, e.g. on the imager chip, may determine which images to discard without analyzing them. For example, if image frames of 64×64 pixels are recorded every 3.2 microseconds, whereas only one frame in 50 microseconds actually contains a cell image and needs to be pushed to the signal processing unit, the required bandwidth may be reduced from 1280 MB/second to an average bandwidth of 82 MB/second. The decision algorithm may decide which images are to be further processed. Since some images do not contain cell information, they are not useful for handling, and a direct decision mechanism to discard those images may considerably speed up the imaging and sorting. This decision may depend on the integrated recorded light response data.

Digital holography can also be applied to analyze the spatial distribution of the polarization state of light transmitted or reflected from objects. This can simply be done by inserting polarization filters in the optical path, for example between the light source and the illuminated object and/or between the illuminated object and the optoelectronic sensing array. Polarization is a known property of the constituents of cells. The polarization-based optical properties of tissues/cells are among the least investigated properties and are gaining more and more attention. Polarization imaging may be used to improve the contrast and differentiate cell types during visualization. Embodiments of the present invention can thus be extended to include polarization analysis by adding polarization filters between the light source and the microfluidic system and between the microfluidic system and the imager.

The method 20 also comprises characterizing 23 the holographic diffraction image obtained for each of the objects when passing through any of the imaging regions in real-time. This characterization takes into account at least one predetermined object type signature. Characterizing 23 may comprise analyzing the scattered light responses recorded in the holographic diffraction images by means of a digital signal processing unit. For example, this characterization may comprise classifying, e.g. with a sorting algorithm, and analyzing the scattered light response with a digital signal processing unit. For example, a digital signal processor may analyze and classify the scattered light responses, wherein the classification comprises a sorting algorithm based on signatures extracted from either non-reconstructed, partially or fully reconstructed digital holograms. Decisions may be taken synchronous with the cell flow. Therefore, a fast classification algorithm may be used on the lens-free images, which can then be used as input for the electrical circuits driving a physical sorter, e.g. a microfluidic switch.

For example, characterizing 23 the holographic diffraction image may comprise comparing the holographic diffraction image with at least one stored reference hologram representing an object type of interest, for example comparing the image to each of a library of pre-stored holograms in order to determine to which object type the object in the holographic diffraction image corresponds. This comparing may comprise calculating, for each at least one stored reference hologram, a correlation measure between the holographic diffraction image on one hand and the stored reference hologram on the other hand, and selecting the object type for which this correlation measure indicates the best correlation. For example, classifying scattered light responses may use a pre-stored library of holograms of interesting cells to classify cells based on a simple comparison of the recorded diffraction pattern with the pre-stored library, e.g. via correlation.

Alternatively, this characterizing 23 of the holographic diffraction image may comprise auto-correlating a plurality of holographic diffraction images in order to identify differences between objects. For example, classifying scattered light responses may use different recorded cell images which are auto-correlated to each other, thereby identifying differences between cells. It is an advantage of such approach that no prior information may be needed.

Characterizing 23 the holographic diffraction image may also comprise performing at least a partial digital spatial reconstruction of the imaged object. For example, a full digital reconstruction of the hologram may be useful if the in-flow imaging capabilities are also used to collect images of cells for further analysis.

The method furthermore comprises steering 24 each object into an outlet, said outlet being selected from a plurality of outlets as a function of the characterization for this object. Thus, sorting of objects, e.g. cells, based on the classification results may be provided by embodiments of the present invention.

According to embodiments of the present invention, the recording 22, characterizing 23 and steering 24 may be performed in parallel for the plurality of microfluidic channels.

In embodiments of the present invention, the method 20 may further comprise a downstream analysis of subpopulations of the objects immersed in a fluid, in which a first sorting may be used as a sample preparation step for the further downstream analysis. Further downstream analysis may comprise high resolution imaging, molecular characterization techniques and 'omics' or sequencing technologies to reveal the genome or proteome information of selected biological cells.

In embodiments of the present invention, the recording 22 may comprise detecting the presence of the object in the flowing medium upstream of the imaging region 4, and the characterizing 23 the holographic diffraction image may be performed in response to the detected presence, e.g. as described above in relation to the first aspect of the present invention. The recording 22 may comprise evaluating whether the object is passing through the imaging region 4.

Characterizing 23 the holographic diffraction image may comprise one or a combination of comparing the holographic diffraction image with at least one stored reference hologram representing an object type of interest, auto-correlating a plurality of holographic diffraction images in order to identify differences between objects and performing at least a partial digital spatial reconstruction of the imaged object.

The recording 22, characterizing 23 and steering 24 may be performed in parallel for a plurality of microfluidic channels 3.

Figure 6:
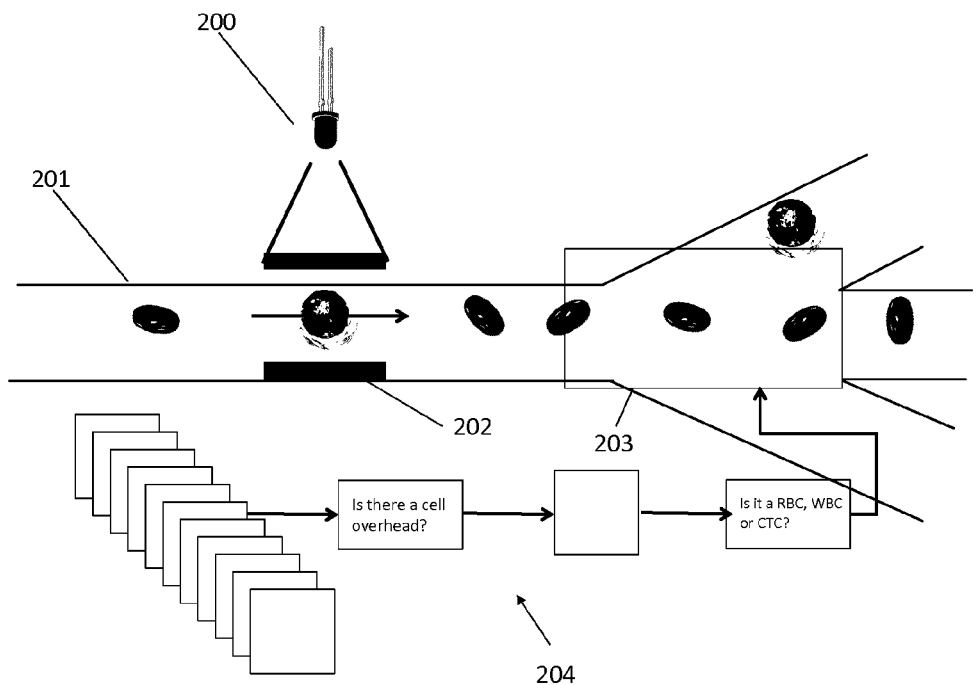
FIG. 6 shows an exemplary application of a method according to embodiments of the present invention.

An exemplary application 204 of a method and system according to embodiments of the present invention is illustrated in FIG. 6. Cells 201 in a blood sample are moving through a microfluidic channel, and, in an imaging region thereof, illuminated by a coherent or partially coherent light source 200, for example a stroboscopically pulsed LED. A holographic imaging element 202 records a holographic diffraction image of the cells 201. This data is then further processed in real-time. For example, an initial evaluation whether an object is present in the imaging region, e.g. captured in the holographic diffraction image, may be performed, for example by dedicated circuitry of the holographic imaging unit. If positive, the data may then be forwarded to a processing unit, which may compare the image to a library of pre-stored reference images, for example corresponding to red blood cell, white blood cell and circulating tumor cell archetypes. Within a predetermined time window, e.g. determined by a path length in the microfluidic system between imaging region and switch, and a predetermined flow speed of the fluid moving in the microfluidic channel, a classification into these categories may be established, and the microfluidic switch of a microfluidic sorting device 203 may be actuated in response to the result, for sorting 203. For example, a white blood cell and a red blood cell may each be diverted into a different output channel, e.g. an outlet.

Several examples and technical considerations will be set forth hereinafter, the present invention not being intended to be limited by such examples and/or technical considerations in any way.

It is an advantage of embodiments of the present invention that a high quality is attainable for an image sensor of limited size. The object under investigation, e.g. a biological cell, inside the micro-fluidic channel, may be located at a certain distance from the light source d1 and from the image sensor d2, both distances d1 and d2 may determine the magnification of the diffraction fringes on the image sensor. At an optimal distance, the reconstruction on an image sensor of limited size may be of the highest quality resulting in the best discrimination of different cell types.

It is an advantage of embodiments of the present invention that good quality information in the holograms and high resolution of the reconstructed images may be obtained. High spatial frequencies, e.g. corresponding to fine features, get spread out the most. When the magnification of the diffraction fringes is optimally covering the pixel matrix, meaning that the fringes covering the important fine features are projected on the active pixel array, the resolution of the hologram is set by the number of pixels in the pixel array. The quality of the information in the holograms and the resolution of the reconstructed images will depend on the size of the blocks used for imaging. There is thus a compromise to be taken with respect to number of pixels to be used to create high resolution holograms while allowing for fast signal processing and object sorting. The specific values may differ depending on the sorting application, as the requirements of the hologram for accurate sorting must be weighed against adequate speed of sorting the objects, e.g. cells.

Where current FACS systems use single pixel detectors (i.e. photomultipliers or avalanche photodiodes) for measurements, in embodiments of the present invention, these single pixel detectors may be replaced by optical CMOS imagers that can take images of cells. The increased spatial resolution to image a cell puts extremely high demands on the real time digital signal processing of the obtained image data. Moreover, imaging multiple (e.g. N) flows at the same time further enlarges the image data set to be processed with a factor N. Such combination of increased spatial resolution and very high throughput may not be known in the current state of the art. Embodiments of the present invention may use a technique known as lens-free or digital holographic imaging to alleviate the requirements on data information to be processed in real time. Light microscopy has traditionally relied on lenses to create microscopic images of small objects. However, lensfree on-chip holographic microscopy takes a digital approach to achieve high-resolution imaging. The light scattered off the cells or micro-organisms interferes with the unscattered portion of the partially-coherent illumination, resulting in hologram recordings of objects without any optical magnification. Moreover, the number of imaging pixels may be strongly reduced compared to a conventional microscope. The resolution of reconstructed images can be digitally increased beyond the resolution determined by the pixel size of the sensor array, e.g. by using so called pixel super-resolution (PSR) techniques to achieve sub-micron lateral resolution.

Therefore, high speed lens-free in-flow cell analysis and sorting for objects in flow, e.g. cells, may be provided by embodiments of the present invention.

The digital holographic microscopy approach relies on a digital recording and reconstruction of diffraction patterns to obtain an image or image signature of the object. Typically (partially) coherent illumination from a small aperture (e.g. an LED in combination with a pinhole, or multiple LED's with pinholes) is used to acquire diffraction patterns from objects on a high resolution optoelectronic sensor array (e.g. a CCD or CMOS camera). The lens-free microcopy produces a hologram of the object with phase information encoded in the diffraction images. Holography was invented over 60 years ago by the physicist Dennis Gabor and is a technique that allows the light scattered from an object to be recorded and later reconstructed. Digital holography uses digital reconstruction of the diffraction patterns. Several reconstruction algorithms are described in literature.

Application to Blood Cell Counting and Sorting

A drop of blood contains a complex mixture of red blood cells, which transport oxygen, and white blood cells (leukocytes) and its subtypes which both battle infections and form an essential element of the immune system, platelets and plasma. Blood counts, counting the total number of each cell population, can be used to indicate the presence of many forms of disease, and therefore are amongst the most commonly performed blood tests in medicine. A nurse collects the sample, drawing the blood into a test tube containing an anticoagulant (EDTA, sometimes citrate) to stop it from clotting. The sample is then transported to a laboratory. Methods such as FACS, fycol gradient and magnetic bead based separation and even manual counting are typically used in the laboratory to count or separate different subtypes of blood cells.

Although the automated analysers give fast, reliable results regarding the number, average size, and variation in size of blood cells, they are not so good to detect cells' shapes which is why manual counting is still used in some cases. Hence, embodiments of the invention presented can be used as a point of care test to replace any of the prior art methods above, to make on the spot blood counts at the point where it is needed.

Many clinical and research applications count or isolate specific white blood cell types for diagnosis and study of disease conditions. An elevated or downregulated amount of any of the subtypes i.e. granulocytes (neutrophils, basophils and eosinophils), monocytes, and lymphocytes (B cells and T cells) may be used to measure and monitor many different health indications including infectious diseases, inflammatory or even cancerous diseases. Moreover, separation and collection of White Blood Cells and Red Blood Cells are typically the first required steps to many different clinical and basic research assays.

For example, the human immunodeficiency virus (HIV) binds to CD4 molecules and thus is able to invade and infect CD4+ T cells. As the disease progresses, the number of CD4+ cells declines below its normal level of about 1.000 per microliter. Embodiments of the present invention can be used to monitor HIV progression on a regular basis at the doctor's office, at the patient's home or in resource limited settings with no access to well-equipped hospital facilities.

For example, white blood cells sense oxidative stress during capillary passage in the body and react by producing reactive oxygen species [Ref: Nature Clinical Practice Cardiovascular Medicine (2008) 5, 811-820]. Conventional FACS is used today in clinical research to determine the number of white blood cells and their level of oxidative stress from patient samples as an indicator of cardiovascular disease. Similar results have been seen to indicate ischemic syndromes and in diabetic conditions.

A high-content high throughput cell sorter according to embodiments of the present invention may enable a wide range of novel applications, particularly those related to isolation of rare biological events. An application with extremely challenging requirements on sorting of rare events, is the detection of circulating tumour cells (CTC's) from whole blood. Traditional cancer therapy is based on the biology of the primary tumour; however, it is usually the tumour dissemination to other parts of the body that results in a negative prognosis and death. For this reason, the detection and characterization of circulating tumour cells (CTC) from blood of cancer patients are believed to be of high prognostic and therapeutic importance. In accordance with embodiments of the present invention, a method is proposed to detect cancer based on classifying and sorting circulating tumour cells (CTC) or cancer related circulating cells (CRCC) from blood in a cell sorting device according to embodiments of the present invention.

CTCs are outnumbered by white blood cells (wbc) in a whole blood sample by a factor of at least 106 and by red blood cells (rbc) with a factor of at least 109. Current detection methods often rely on a phenotypic characterization requiring an initial magnetic bead based cell enrichment technique followed by microscopic analysis of the cell phenotype. While currently considered the standard for CTC analysis, these techniques are cumbersome, require expertise and remain subjective to a certain extent.

An excellent review on the different techniques used for enumeration and molecular detection of circulating tumour cells as a means for cancer diagnostics is presented in [Cancers 2010, 2, 1236-1250]. The current gold standard is the CellSearch™ technology and employs a ferrofluid consisting of magnetic nanoparticles coated with antibodies targeting EpCAM, an epithelial marker. After immunomagnetic capture and enrichment, cells are fixed and stained with fluorescent probes (e.g. DAPI, and antibodies to cytokeratins and CD45) to identify and enumerate CTCs. The CellTracks™ Analyzer, an automated high resolution fluorescence microscope acquires images and displays a gallery of images of morphology and fluorescent stainings for final classification by a trained analyst. Sensitivity is in the order of 1 CTC per 7.5 mL of whole blood.

Isolation by size (for example, as is done in the ISET by ScreenCell) allows direct enrichment of epithelial cells using size exclusion thereby reducing the dependence for detection on the expression of a selected set of epithelial markers. Peripheral blood is diluted with ISET buffer, loaded onto membranes with 8 μm calibrated pores [Vona, G et al. Am. J. Pathol. 2000, 156, 57-63.]. The majority of leukocytes are small enough to flow through the pores whereas larger tumour cells are captured on the membrane. The technique minimizes the risk of losing circulating tumour cells by avoiding of immuno-labeling with epithelial specific antibodies.

Current CTC detection evaluates diagnostic or therapeutic tumour markers (on DNA, mRNA or protein level) based on a biased pre-selected set of CTC using e.g. epithelial markers or size. In fact, there is no epithelial marker known to be uniformly expressed by all cancer types, even EpCAM is not expressed in 100% of tumour types, but only in 70-80% of variable cancer types [Went et al. Hum. Pathol. 2004, 35, 122-128]. The process of EMT (epithelial to mesenchymal transition) postulated by some as required for metastasis, involves phenotypic changes in a subset of cells during which epithelial cells become more invasive. One therefore could expect that CTCs with metastatic potential are intrinsically heterogeneous and the current cell enrichment techniques create always a bias to some extent.

The high content high throughput cell imager and sorter described in accordance with embodiments of the present invention may be used for cancer detection. Patient blood samples or diluted patient blood samples can be introduced into the system. CTC's or cancer related circulating cells are counted based on the holographic images taken in the system. A method according to embodiments of the present invention does not introduce any bias and sorts based on user set parameters. Accurate detection of the CTC count from patient blood using the current imager/sorter can be used as a diagnostic method or therapy follow up method in clinical practice of cancer management.

One implementation in the case of sorting very rare cells is to use a cascade system, e.g. a trapped system, in which a first rough sorting is made for example to discriminate between cells which are very different from CTC's (such as separation of red blood cells from white blood and white blood resembling cells) and a second, third etc. sorting event may refine the sorting upon other properties such as size and morphology of leukocytes and CTC's. The technique is non-destructive and iterated analysis is possible by reintroducing the sample in to the system as a means to confirm results. If the images are used to sort the cells, cells can subsequently be used for molecular characterization. Subpopulations can also be reintroduced into the system in order to confirm results or to do subsequent sorting based on a different parameter or different staining.

Other applications that can benefit from embodiments of the present invention can include isolation or sorting of other rare cells from blood, such as for example heterogeneous stem cell populations, sorting of foetal cells from maternal blood.

Furthermore, in another application example, early pathogen detection is extremely important to avoid outbreak of certain diseases or as a means to decide on which therapy to use. Promptness of pathogen detection and the appliance of appropriate antibiotics are currently the cornerstones of treating bacterial infections, but cannot treat viral infections. However, resistance to antibiotics is an increasing public health problem that can be attributed largely to their overuse. It becomes therefore more important to detect and identify pathogens as early as possible so that the most appropriate therapies can be started up in time.

Whereas bacteria have typically the size of a single cell, viruses have sizes of about 100 nm, this is too small to be seen by a conventional microscope. They cannot multiply on their own, so they have to invade a 'host' cell and take over its machinery in order to be able to make more virus particles. Vaccines and an increasing number of antiviral remedies are being developed that prevent the virus multiplying and cause the illness to run its course more quickly.

Currently, blood culture is the gold standard method for pathogen detection in patients suspected of systemic infections. The detection methods are typically twofold: 1) biochemical and microscopic analysis of the cell cultures and 2)

DNA/RNA tests to be performed on these cell cultures to identify the infection. It usually takes 3 to 5 days to obtain a result from blood culture, which is too late to initiate an effective therapy. Fluorescent active cell sorting (FACS) has been used as a tool to study the cellular immune response to pathogens, more specifically to discriminate and count infected cells versus non infected cells as well as the effect of different treatments including vaccine agents on these cells. For bacteria it is also possible to use FACS for direct sorting of the bacteria, since bacteria have similar size to cells. Viruses are considered too small for being sorted by current FACS systems.

There are several reasons why existing FACS or in-flow imaging systems are not being used as a routine clinical analysis tool. The establishment of the high throughput high content cell imager and sorter would have clear advantages for detection of pathogens in patient samples, but also in food or environmental samples such as drinking water.

The first is the risk of contamination of the FACS or imaging system by the pathogens present in the sample. Indeed, current FACS systems are very expensive tools, where typically none of the components is implemented as a disposable. This is the reason why centralized FACS core facilities often refuse to analyze samples which are potentially contaminated by hazardous pathogens. In embodiments of the present invention, the fluid handling system may be designed as a disposable and no contamination between different samples can occur. No false positives as a result of contamination can result.

The second advantage of embodiments of the present invention is that the advanced imaging analysis features allow the direct identification of bacteria present in samples by analyzing the morphology of the bacteria themselves. Bacteria come in wide variety of sizes and shapes, including rods, spherical, comma-like, bacteria with large flagella and elaborately branched structures. Some of them form flocks or long filaments. The holographic images taken by the high content imager are especially sensitive to edges and therefore extremely suited to distinguish different morphologies. The high content imager can thus identify bacterial infections in biospecimen, based on the recognition of the morphology of the bacteria and the counting of the number of bacteria units. Since bacteria grow by division, forming colonies over time, embodiments of the present invention may also be used to estimate the colony size of the colony forming units and to predict the bacteria growth curve.

FACS and fluorescent confocal imaging are methods typically used for counting and analyzing the response of infected versus non-infected host cells, in which the viral infection is made visible via a fluorescent marker such as a FITC labeled antibody or fluorescent protein. The high content imager/sorter according to embodiments of the present invention provides more spatial information on the location of the fluorescent markers. Moreover, since holographic imaging has proven to be quite efficient for imaging smaller objects it may be possible to also count and perhaps identify viruses directly without fluorescent markers. An entire field of research is dedicated to superresolution methods to overcome Abbe's optical diffraction limit in digital holographic microscopy using tricks such as off axis illumination, engineered apertures and the use of time information to get more spatial information. The imaging and sorting method according to embodiments of the present invention can also be extended to image very small objects such as viruses by replacing the LED or laser by a deep UV or even X-Ray (partially) coherent light source for illumination.

In yet a further application, bioprocessing technology uses living cells (including yeast and bacteria) to manufacture products such as fine chemicals, antibodies, recombinant proteins, vaccines, but also fermentation based products including wine and beer. The goal of process monitoring systems is generally to achieve better and consistent production yields, to minimize batch-to-batch variation, and to receive early warnings of the potential failure, contamination or unacceptability of an evolving batch, for example because of contamination by foreign microorganisms. Important variables for the control of such processes are cell count, cell-size distribution and the morphology of cells. Another example uses protein crystallization size and morphology measurements to monitor the process. Although parameters like pH, temperature and oxygen content can be monitored online, current process monitoring methods at the cell level typically still include manual sampling and conventional microscopic analysis which is a quite tedious process. Online measurement methods, including biosensors and biomass measurement methods, are being developed but may include example problems such as fouling and drift, which limit the accuracy and duration of use.

Possible in situ imaging methods for bioprocess monitoring in bioreactors are described in Anal Bioanal Chem. 2010 November; 398(6):2429-38 and the following description is based on this article. The sensor is immersed directly in the medium during the whole process and images are taken at intervals without interrupting the process. The frequency at which images are acquired depends on the biological process. For monitoring of mammalian cells an hourly time interval is sufficient and for monitoring of bacteria a minute cycle should be chosen to obtain relevant analytical information for the process. After image acquisition the data set is analyzed with sophisticated image-analysis algorithms. Information about the cell size, morphology, and other relevant variables can be used for process control. All described systems include a source (LED or laser, sometimes fibre based) a lensing system or objective lens and a CCD camera, they all use conventional reflection based imaging methods. The sampling zone in the bioreactor is typically defined either by the depth of focus of the conventional optical microscope or by a mechanical sampling device such as a slider that moves to take a new sample from the bioreactor. In both cases, the imaging is static and does not imply flowing cells or microorganisms.

Two in situ imager implementations, one by Joeris K, Frerichs J G, Konstantinov K, Scheper T (2002) Cytotech 38:129-134 and one by Camisard V, Brienne J P, Baussart H, Hammann J, Suhr H (2002) BiotechnolBioeng 78:73-80) describe a transmission based bright field imager, but both still use conventional imaging methods using an objective lens and an objective tube to collect the light coming from the object and focus it on the CCD camera system. Finally an experimental flow-through microscopic system is described for parallel monitoring of cell densities [Journal of Biotechnology Volume 150, Issue 1, 1 Oct. 2010, Pages 87-93]. This system uses for the first time a flow cell for continuous monitoring but the imager is similar as the in situ imagers described above.

The device according to embodiments of the present invention may be implemented in different possible locations with respect to bioreactors:

Continuous monitoring in a bypass stream that continuously samples the bioreactor, allowing the optical system to remain outside of the bioreactor.

Continuous monitoring in a microfluidic disposable which is part of the bioreactor wall for instance if the bioreactor itself is meant to be made from disposable materials.

Continuous monitoring inside the bioreactor similar to existing inline methods.

Continuous monitoring inside the bioreactor at several places; because holographic imagers are fairly compact, multiple monitors could be used in a large reactor vessel, so that a more complete measurement will be taken and results are less dependent on process parameters such as mixing.

In case of microfluidic bioreactors, the imaging system can be implemented as part of the fluidic handling system of the bioreactor.

Sorting according to embodiments of the present invention can also be used to image and sort objects where object shape and diffraction pattern is important for discrimination of subpopulations. Examples are:

Sorting of crystals, e.g. protein crystals that can be formed in microfluidic systems.

Sorting of nanoparticles e.g. a polydisperse particle sample.

Sorting of nanoparticles which are part of nanoparticle assay.

For example, nanoparticles are often used to make affinity binding reactions (such as antibodies and its corresponding antigen or DNA complementary strands) thereby recognizing the presence of an analyte in a solution. By sorting and counting individual particles from clusters of particles, one can measure the bound fraction in the solution.

The invention claimed is:

1. A device configured to sort objects immersed in a flowing medium, the device comprising:
   a holographic imaging unit including a CMOS or CCD image sensor partitioned into a plurality of holographic imaging elements configured to provide a plurality of holographic diffraction images, wherein each imaging element comprises an array of imaging pixels;
   a fluid handling unit including an imaging region and a switch arranged downstream of the imaging region, wherein the fluidic handling unit is configured to conduct the flowing medium along a corresponding holographic imaging element in the imaging region, and wherein the switch is configured to direct one or more objects in the flowing medium to one or more outlets of a plurality of outlets; and
   a processor configured to:
      based on at least one holographic diffraction image of the plurality of holographic diffraction images, determine a real-time characterization of the one or more objects that pass through the imaging region; and
      in response to the real-time characterization, control the switch to direct the one or more objects in the flowing medium to the one or more outlets.

2. The device according to claim 1, wherein the image sensor is configured for parallel readout of the plurality of imaging elements thereby providing the plurality of holographic diffraction images simultaneously and independently from each other.

3. The device according to claim 1, further comprising a detector unit configured to generate a trigger signal that is representative of a detected presence of the one or more objects in the flowing medium upstream of the imaging region.

4. The device according to claim 3, wherein the detector unit comprises a photodetector configured to receive light modulated by moving objects, or at least one electrode configured to detect a change in an electrical signal caused by moving objects.

5. The device according to claim 3, wherein the processor is configured to determine the real-time characterization of the one or more objects based on the trigger signal and on the at least one holographic diffraction image.

6. The device according to claim 3, wherein the holographic imaging elements are configured to provide the holographic diffraction images in response to the trigger signal.

7. The device according to claim 3, wherein the detector unit is upstream from the imaging region.

8. The device according to claim 1, wherein the holographic imaging elements are configured to:
   evaluate a detection criterion related to detecting the presence of the one or more objects in the flowing medium, and
   responsive to the detection criterion being satisfied, transmit the holographic diffraction images to the processor.

9. The device according to claim 1, further comprising at least one flow monitoring device configured to provide flow information relating to at least one of a velocity or an acceleration of the one or more objects in the flowing medium, and wherein the processor is configured to, responsive to the flow information and the real-time characterization, control the switch to direct the one or more objects in the flowing medium to the one or more outlets.

10. The device according to claim 9, wherein the processor is configured to:
   determine, responsive to the flow information, a predicted time of arrival of the one or more objects in at least one of the imaging region or at the switch; and
   control, responsive to the predicted time of arrival, at least one of the one or more holographic imaging elements to provide the holographic diffraction images, or the switch to direct the one or more objects in the flowing medium to the one or more outlets.

11. The device according to claim 1, wherein the fluid handling unit further comprises a focusing unit configured to concentrate the one or more objects in a central region of the flowing medium through the imaging region, and wherein the focusing unit includes a channel dimensioned to twice the size of the objects in the flowing medium.

12. The device according to claim 1, wherein the fluid handling unit includes a plurality of microfluidic channels configured to conduct the flowing medium along the imaging region and to the switch.

13. The device according to claim 1, wherein the imaging region is arranged at an angle with respect to a grid alignment of a respective image sensor, and wherein the processor is further configured to receive a plurality of holographic diffraction images from the holographic imaging unit, and to construct a super-resolution holographic diffraction image from the plurality of holographic diffraction images obtained for the one or more objects in the flowing medium.

14. A method comprising:
   introducing a flow of a fluid into one or more channels, wherein the one or more channels include an imaging region;
   recording, using a CMOS or CCD image sensor, a plurality of holographic diffraction images of one or more objects in the fluid as the one or more objects pass through the imaging region, wherein the image sensor is partitioned into a plurality of holographic imaging elements, and each imaging element comprising an array of imaging pixels;

characterizing the one or more objects in the plurality of holographic diffraction images wherein a characterization of each object accounts for at least one predetermined object type signature; and based on the characterization of each object, directing the one or more objects into one of a plurality of outlets.

15. The method according to claim 14, wherein the recording of the plurality of holographic diffraction images further comprises parallel readout of the imaging elements thereby providing the plurality of holographic diffraction images simultaneously and independently from each other.

16. The method according to claim 14, further comprising generating a synchronization signal that is representative of a detected presence of one or more objects in the fluid upstream of the imaging region, wherein characterizing the one or more objects is performed responsive to the synchronization signal.

17. The method according to claim 16, wherein recording the plurality of holographic diffraction images is performed in response to the synchronization signal.

18. The method according to claim 14, further comprising monitoring the flowing fluid to provide flow information relating to at least one of a velocity or an acceleration of the one or more objects in the fluid, wherein directing the one or more objects into one of a plurality of outlets is performed responsive to the flow information and the characterization of the one or more objects.

19. The method according to claim 18, further comprising:

determining, responsive to the flow information, a predicted time of arrival of the one or more objects in at least one of the imaging region or at a switching region, wherein objects are directed into one of a plurality of outlets from the switching region; and controlling, responsive to the predicted time of arrival, at least one of the recording of the plurality of holographic diffraction images, or the directing of the one or more objects into one of a plurality of objects.

20. The method according to claim 14, wherein the one or more channels includes a focusing unit configured to concentrate the one or more objects in a central region of the flowing fluid through the imaging region, wherein the focusing unit includes a channel dimensioned to twice the size of the objects in the fluid.

* * * * *